(12) United States Patent
Beaudoin et al.

(10) Patent No.: US 6,617,439 B1
(45) Date of Patent: Sep. 9, 2003

(54) C8-SUBSTITUTED PURINE NUCLEOTIDE ANALOGS

(75) Inventors: Adrien R. Beaudoin, Rock Forest (CA); Fernand-Pierre Gendron, Trois-Rivières (CA); Efrat Halbfinger, Raanama (IL); Bilha Fischer, Shoham (IL)

(73) Assignees: Bar-Ilan University, Ramat Gen (IL); Universite de Sherbrooke, Sherbrooke (CA)

( * ) Notice: Subject to any disclaimer, the term of this patent is extended or adjusted under 35 U.S.C. 154(b) by 0 days.

(21) Appl. No.: 09/591,177

(22) Filed: Jun. 9, 2000

(51) Int. Cl.$^7$ .................. C07H 21/02; C07H 21/00; C12N 1/68
(52) U.S. Cl. .................. 536/23.1; 435/6; 435/91.1; 536/25.3
(58) Field of Search .................. 435/6, 91.1, 91.2, 435/183, 287.2; 536/23.1, 25.3

(56) References Cited

U.S. PATENT DOCUMENTS 6,312,662 B1 * 11/2001 Erion et al. .................. 424/9.1

OTHER PUBLICATIONS

Gendron et al., "ATP diphosphohydrolase inhibitors: novel perspectives," *Poster Abstract*, p. 327 from conference Ecto–ATPases and Related Ectonucleotidases (Jun. 12, 1999).
p. 1072 Sigma–Aldrich catalogue "Bioactive Peptides."
Burnstock, G., Campbell, G., Bennett, M., and Holman, M.E., Innervation of the Guinea–Pig Taenia Coli: are there intrinsic inhibitory nerves which are distinct from sympathic nerves? Int. J. Neuropharmacol 3: 163–166, 1964.
Burnstock, G. Evolution of the autonomic innervation of visceral and cardiovascular systems in vertebrates. Pharmacol. Rev. 21 (4): 247–324, 1969.
Su, C., Bevan, J.A., and Burnstock, G. [3H] adenosine triphosphate: release during stimulation of enteric nerves. Science 173(994): 336–338, 1971.
Langer, S.Z., and Pinto, J.E.B. Possible involvement of a transmitter different from norepinephrine in the residual responses to nerves stimulation of the cat nictitating membrane after pretreatment with reserpine. J. Pharmacol. Exp. Ther. 196(3): 697–713, 1976.
Burnstock. G. Purinergic receptors. J. Theor. Biol. 62 (2): 491–503, 1976.
Von Kugelgen, I., and Starke, K. Noradrenaline–ATP co–transmission in the sympathetic nervous system. Trends Pharmacol. Sci. 12(9): 319–324, 1991.
Westfall, D.P., Sedaa, K.O., Shinozuka, K., Bjun, R.A., and Buxton, I.L. ATP as a Cotransmitter Ann. NY Acad. Sci. 603: 300–310, 1990.
Burnstock, G. Neural nomenclature. Nature 229(5282): 282–283, 1971.

Burnstock, G. A basis for distinguishing two types of purinergic receptors. In: Cell membrane receptors for drugs and hormones: A multidisciplinary approach. (Eds. R.W. Straub and L. Bolis), Raven press, New York. Pp. 108–118, 1978.
Fredholm, B.B., Abbracchio, M.P., Burnstosk, G., Daly, J.W., Harden, T.K., Jacobson, K.A., Leff, P., and Williams, M. Nomenclature and classification of purinoceptors. Pharmacol. Rev. 46(2): 143–156, 1994.
Juul, B., Plesner, L., and Aalkjaer, C. Effects of ATP and related nucleotides on the tone of isolated rat mesenteric resistance arteries. J. Pharmacol. Exp. Therap. 264: 1234–1240, 1993.
Motte, S.; Commun, D.; Pirotton, S.; Boeynaems, J.M. Involvement of multiple receptors in the actions of extracellular ATP: the example of vascular endothelial cells. Int. J. Biochem. Cell Biol. 27: 1–7, 1995.
Rongen, G.A., Floras, J.S., Lender, J.W.M, Thier, T., and Smits, P. Cardiovascular pharmacology of purines. Clin. Sci. 92: 13–24, 1997.
Dubyak, G.R., and El Moatassim, C. Signal transduction via P2–purinergic receptors for extracellular ATP and other nucleotides. Am. J. Physiol. 265: C577–C606, 1993.
Johnson, C.R., and Hourani, S.M. Contractile effects of uridine 5'–triphosphate in the rat duodenum. Br. J. Pharmacol. 113(4): 1191–1196, 1994.
Pennanen, M.F., Bass, B.L., Dziki, A.J., and Harmon, J.W. Adenosine differential effect on blood flow to suregions of the upper gastrointestinal tract. J. Surg. Res. 56(5): 461–465, 1994.
Strohmeier, G.R., Reppert, S.M., Lencer, W.I., and Madana, J.L. The A2b adenosine receptor mediated cAMP responses to adenosine receptor agonists in human intestinal epithelia. J.Biol. Chem. 270(5): 2387–2394, 1995.
Hancock, D.L., and Coupar, I.M. Functional characterization of the adenosine receptor mediating inhibition of peristalsis in the rat jejunum. Br. J. Pharmacol 115(5):739–744, 1995.
Sarna, S.K. Gastrointestinal longitudinal muscle contractions. Am. J. Physiol. 265(1pt1): G156–G164, 1993.
Baricordi, O.R., Ferrari, D., Melchiorri, L., Chiozzi. P., Hamann, S., Chiair, E., Rubini, M., and Di Virgilio, F. An ATP–activated channel is involved in mitogenic stimulation of human T lymphocytes. Blood 87(2): 682–690, 1996.

(List continued on next page.)

Primary Examiner—Bradley L. Sisson
(74) Attorney, Agent, or Firm—Quarles & Brady LLP

(57) ABSTRACT

C8-substituted purine nucleotide analogs, such as ATP analogs, and their use is described, including their use as inhibitors of NTPDases and thereby as tools to modulate the conversion of nucleotides into nucleoside derivatives, and thus modulate the levels of these compounds. Such modulation further provides for the modulation of the activity and function of many processes which are affected by these compounds.

3 Claims, 8 Drawing Sheets

OTHER PUBLICATIONS

Di Virgilio, F. The P2Z purinoceptor: an intriguing role in immunity, inflammation and cell death. Immunol. Today 16(11):525–528, 1995.

Ventura, M.A., and Thomopoulos, P. ADP and ATP activate distinct signaling pathways in human promonocytic U–937 cells differentiated with 1,25–dihydroxy–vitamin D3. Mol. Pharmacol 47: 104–114, 1995.

Biffen, M., and Alexander, D.R. Mobilization of intracellular Ca2+ by adenine nucleotides in human T–leukaemia cells: evidence for ADP–specific and P2y–purinergic receptors. Biochem. J. 304:769–774, 1994.

Apasov, S., Koshiba. M., Redegeld, F., and Sitokovsky, M.V. Role of extracellular ATP and P1 and P2 classes of purinergic receptors in T–cell development and cytotoxic T lymphocyte effector functions. Immunol. Rev. 146: 5–19, 1995.

Hedge, S.S., Mandel, D.A., wilfird, M.R., Briand, S., Ford, A.P.D.W., and Eglen, R.M. Evidence for purinergic neurotransmission in the urinary bladder of pithed rats. Eur. J. Pharmacol. 349(1): 75–82, 1998.

Dunwiddie, T.V., Abbracchio, M.P., Bischofberger, N., Brundege, J.M., Bruell, G., Collo, G., Corsi, C., Diao, L., Kawashima, E., Jacobson, K.A., Latini, S., Lin, R.C.S., Noth, R.A., Pazzagli, M., Pedata, F., Pepen, G.C., Proctor, W.R., Rassendren, F., Surprenant, A., and Cattabeni, F. Purinoceptors in the central nervous system. Drug Dev. Res. 39(3–4): 361–370, 1996.

Burnstock, G., and Wood, J.N. Purinergic receptors: Their role in nociception and primary afferent neurotransmission. Curr. Opinion in Neurobiol. 6(4): 526–532, 1996.

Von Kugelgen, I. Purinoceptors modulating the release of noradrenaline. J. Autonomic. Pharmacol. 14(1): 11–12, 1994.

Beaudoin, A.R.: Sévigny, J.; Picher, M. ATP diphosphohydrolases, apyrases and nucleotide phosphohydrolases: biochemical properties and functions. In: Biomembrane, vol. 5; Lee, A.G., Ed.; Greenwich, CT: JAI, pp. 369–401, 1996.

Beaudoin, A.R.; Grondin, G.; Enjyoji, K.; Robson, S.C.; Sévigny, J.; Fischer, B.; Gendron, F.–P. Physiological role of NTPDases (ATP diphosphohydrolases) in mammals. Proceeding of the 2nd International Workshop on ecto–ATPase and related nucleotidases. Diepenbeek, Belgium, Jun. 14–18, 1999. Vanduffel L., and Lemmens R., Eds. Shaker Publishing B.V., The Netherlands; pp. 125–135, 2000.

Plesner, L. Ecto–ATPases: identities and functions. Int. Rev. Cytol. 158: 141–214, 1995.

Vlajkovic, S.M.; Thorne, P.R.; Hously, G.D.; Munoz, D.J.B.; Kendrick, I.S. Ecto–nucleotidases terminate purinergic signalling in the cochlear endolymphatic compartment. Neuroreport 9: 1559–1565, 1998.

Zimmermann, H. 5'–Nucleotidase: molecular structure and functional aspects. Biochem. J. 285: 345–365, 1992.

Laliberté, J.F., and Beaudoin AR. Sequential hydrolysis of the gamma– and beta–phosphate groups of ATP by the ATP diphosphohydrolase from pig pancreas. Biochim. Biophys Acta. 742(1):9–15, 1983.

Côté Y.P., Pavate C. and Beaudoin A.R. The control of nucleotides in blood vessels: Role of the ATP diphosphohydrolase (apyrase). Curr. Top. Pharmacol. 1: 83–92, 1992.

Sévigny J., Levesque F.R., Grondin G. and Beaudoin A.R. Purification of the blood vessel ATP diphosphohydrolase, identification and localization by immunological techniques. Biochim. Biophys. Acta 1334: 73–88, 1997.

LeBel D., Poirier G.G. Phaneuf, S. St–Jean P., Laliberté, J.–F. and Beaudoin A.R. Characterization and purification of a calcium sensitive ATP diphosphohydrolase from the pig pancreas. J. Biol. Chem. 255: 1227–1233, 1980.

Sévigny, J.; Côté, Y.P.; Beaudoin, A.R. Purification of pancreas type I ATP diphosphohydrolase and identification by affinity labelling with 5'–p–fluorosulfonyl benzoyl adenosine ATP analog. Biochem. J. 312: 351–356, 1997. 50.

Christoforidis, S.; Papamarcaki, T.; Galaris, D.; Kellner, R.; Tsolas, O. Purification and properties of human placental ATP diphosphohydrolase. Eur. J. Biochem. 234: 66–74, 1995.

Kaczmarek, E.,; Koziack, K.; Sévigny, J.; Siegel, J.B.; Anrather, J.; Beaudoin, A.R.; Bach, F.H.; Robson, S.C. Identification and characterization of CD39/vascular ATP diphosphohydrolase. J. Biol. Chem. 271: 33116–33122, 1996.

Maliszewski, C.R.; Delespesse, G.L.; Schoenborn, M.A.; Armitage, R.J.; Fanslow, W.C.; Nakajima, T.; Baker, E.; Sutherland, G.R.; Poindexter, K.; Birks, C.; Alpert, A.; Friend, D.; Gimpel, S.D.; Gayle III, R.B. The CD39 lymphoid cell activation antigen: Molecular cloning and structural characterization. J. Immunol. 153: 3574–3583, 1994.

Wang, T.F.; Guidotti, G. CD39 is an ecto–(Ca2+, Mg2+)–apyrase. J. Biol. Chem. 271: 9898–9901, 1996.

Barcellos, C.K. Schetinger MR. Battastini AM. Silva LB. Dias RD. Sarkis JJ. Inhibitory effect of cadmium acetate on synaptosomal ATP diphosphohydrolase (EC 3.6.1.5; apyrase) from adult rat cerebral cortex. Br. J. Med and Biol. Res. 27(5):1111–1115, 1994.

Côté, Y.P., Ouellet, S., and Beaudoin, A.R. Kinetic properties of type–II ATP diphosphohydrolase from the tunica media of the bovine aorta. Biochim. Biophys. Acta 1160(3): 246–250, 1992.

Picher, M.; Sévigny, J.; D'Orléans–Juste, P.; Beaudoin, A.R. Hydrolysis of P2–purinoceptor agonists by a purified ecto–nucleotidase from the bovine aorta, the ATP diphosphohydrolase. Biochem. Pharmacol. 51: 1453–1460, 1996.

Westfall, T.D., Kennedy, C., and Sneddon, P. The ecto–ATPase inhibitors ARL 67156 enhance parasympathetic neurotransmission in the guinea–pig urinary bladder. Eur. J. Pharmacol. 329(2–3): 169–173, 1997.

Crack, B.E., Pollard, C.E., Beukers, M.W., Roberts, S.M., Hunt, S.F., Ingall, A.H., McKechnie, K.C., Ijzerman, A.P., and Leff, P. Pharmacological and biochemical analysis of FPL 67156, a novel, selective inhibitor of ecto–ATPase. Br. J. Pharmacol. 114(2): 475–481, 1995.

Chen, B.C., Lee, C.M., and Lin W.W. Inhibition of ecto–ATPase by PPADS, suramin and reactive blue in endothelial cells, C–6 glioma cells and raw 264.7 macrophages. Br. J. Pharmacol. 119(8): 1628–1634, 1996.

Kennedy, C., Westfall, T.D., and Sneddon, P. Modulation of purinergic neurotransmission by ecto–ATPase. Sem. Neurosci. 8(4) : 195–199, 1996.

Fischer, B.; Chulkin, A.; Boyer, J.L.; Harden, K.T.; Gendron, F.–P.; Beaudoin, A.R.; Chapal, J.; Hillaire–Buys, D.; Petit, P. 2–thioether–5'–O–(1–thiotriphosphate) adenine derivatives as new insulin secretagogues acting through P2Y–receptors. J. Med. Chem. 42: 3636–3646, 1999.

Bültmann, R., Wittenburg, H., Pause, B., Kurz, G., Nickel, P., and Starke, K. P2–purinoceptors antagonists: III. Blockade of P2–purinoceptor subtypes and ecto–nucleotidases by compounds related to suramin. Naunyn–Schmiedeberg's Arch. Pharmacol. 354: 498–504, 1996.

Tuluc, F., Bültmann, R., Glänzel, M., Wilhelm Frahm, A., and Starke, K. P2–receptor antagonists: IV. Blockade of P2 receptor subtypes and ecto–nucleotidases by compounds related to reactive blue 2. Naunyn–Schmiedeberg's Arch. Pharmacol. 357: 111–120, 1998.

Bëltmann, R., and Starke, K. Reactive red 2: a P2Y–selective purinoceptor antagonist and an inhibitor of ecto–nucleotidase. Naunyn–Schmiedeberg's Arch. Pharmacol. 352: 477–482, 1995.

Wittenburg, H., Bültmann, R., Pause, B., Ganter, C., Kurz, G., and Starke, K. P2–purinoceptor antagonists: II. Blockade of P2–purinoceptor subtypes and ecto–nucleotidases by compounds related to Evans Blue and trypan blue. Naunyn–Schmiedeberg's Arch. Pharmacol. 354: 491–497, 1996.

Bültmann, R., Pause, B., Wittenburg, H., Kurz, G., and Starke, K. P2–purinoceptor antagonists: I. Blockade of P2–purinoceptor subtypes and ecto–nucleotidases by small aromatic isothiocyanato–sulphonates. Naunyn–Schmiedeberg's Arch. Pharmacol. 354: 481–490, 1996.

Bonan, C.D., Battastini, A.M.O., Schetinger, M.R.C., Moreira, C.M., Frassetto, S.S., Dias, R.D., and Sarkis, J.J.F. Effects of 9–amino–1,2,3,4–tetrahydroacridine (THA) on ATP diphosphohydrolase (EC 3.6.1.5) and 5' nucleotidases (EC 3.1.3.5) from rat brain synaptosomes. Gen. Pharmac. 28(5): 761–766, 1997.

Gendron F.–P., Halbfinger E., Fischer B., D'Orleans–Juste P., Duval M. and Beaudoin, A. R. Novel ATP diphosphydrolase inhibitors: Synthesis, biochemical and pharmacological characterization. J. Med. Chem., 2000. (in press).

Fischer, B.; Boyer, J.L.; Hoyle, C.H.; Ziganshin, A.U.; Brizzolara, A.L.; Knight, G.E.; Zimmet, J.; Burnstock, G.; Harden, T.K.; Jacobson, K.A. Identification of potent, selective P2Y–purinoceptor agonists: structure–activity relationships for 2–thioether derivatives of adenosine 5'–triphosphate. J. Med. Chem. 36: 3937–3946, 1993.

Baykov A.A., Evtushenko O.A. and Avaeve S.M. Malachite green procedure for orthophosphate determination and its use in alkaline phosphatase–based enzyme immunoassay. Anal. Biochem. 171: 266–270, 1988.

Bradford M.M. A rapid and sensitive method for the quantification of microgram quantities of protein utilising the principle of protein–dye–binding. Anal. Biochem. 72: 248–254, 1976.

Berthiaume, N.; Claing, A.; Regoli, D.; Warner, T.D.; D'Orléans–Juste, P. Charaterization of receptors for kinins and neurokinins in the arterial and venous mesenteric vasculatures of the guinea–pig. Br. J. Pharmacol. 115: 1319–1325, 1995.

Halbfinger, E.; Major, D.T.; Ritzmann, M.; Ubl, J.; Reiser, G.; Boyer, J.L.; Harden, K.T.; Fischer, B. Molecular recognition of modified adenine nucleotides by the P2Y1–receptor. Part I. A synthetic, biochemical, and NMR approach. J. Med. Chem. 42: 5325–5337, 1999.

Major, D.T.; Halbfinger, E.; Fischer, B. Molecular recognition of modified adenine nucleotides by the P2Y1–receptor. II. A computational approach. J. Med. Chem. 42: 5338–5347, 1999.

Van Rhee, A.M.; Fischer, B.; Van Galen, P.J.M.; Jacobson, K.A. Modelling the P2Y purinoceptor using rhodopsin as template. Drug Design and Delivery 13: 133–154, 1995.

Hirst, G.D.S.; Jobling, P. The distribution of g–adrenoceptors and P2 purinoceptors in mesenteric arteries and vains of theguinea–pig. Br. J. Pharmacol. 96: 993–999, 1989.

Onaka, U.; Fujii, K.; Abe, I.; ;Fujishima, M. Enhancement by exogenous and locally generated angiotensin II of purinergic neurotransmission via angiotensin type 1 receptor in the guinea–pig isolated mesenteric artery. Br. J. Pharmacol. 122: 942–948, 1997.

Fujii, K. Evidence for adenosine triphosphate as an excitatory transmitter in guinea–pig, rabbit and pig urinary bladder. J. Physiol. 404: 39–52, 1989.

Ishikawa, S. Actions of ATP and alpha,beta–methylene ATP on neuromuscular transmission and smooth muscle membrane of the rabbit and guinea–pig mesenteric arteries. Br. J. Pharmacol. 86: 777–787, 1985.

* cited by examiner 1 a : X = S, Y = O, Z = O, n = 0
b : X = O, Y = CH₂, Z = O, n = 1
c : X = O, Y = O, Z = CH₂, n = 1
d : X = S, Y = CH₂, Z = NH, n = 1

2 a : n = 1, X = S
b : n = 0, X = S
c : n = 1, X = NH
d : n = 1, X = O 3. n = 1, a : R = hexyl, b : R = benzyl
4. n = 0, a : R = hexyl, b : R = benzyl 5 a : Ar = p-NO₂-C₆H₄
b : Ar = p-NH₂-C₆H₄

6. X = S
7. X = NH
8. X = O

| Substrates | | Km (μM) | Vmax (μmol/min/mg protein) | Inhibitors | | Ki (μM) |
|---|---|---|---|---|---|---|
| ATP | | 18 ± 1 | 1.65 ± 0.10 | 8-cycloheptylS-ATP | 6a | 31 ± 2.5 |
| ADP | | 33 ± 1 | 1.30 ± 0.08 | 8-CH2tBuS-ATP | 6b | 45 ± 2.5 |
| 2-BuS-ATP | 2a | 36 ± 6 | 0.83 ± 0.05 | 8-hexylS-ATP | 6d | 16 ± 2.0 |
| 2-BuS-ADP | 2b | 63 ± 14 | 0.94 ± 0.10 | 8-BuS-ATP | 6e | 10 ± 2.0 |
| 2-BuNH-ATP | 2c | 32 ± 8 | 0.99 ± 0.10 | | | |
| 2-BuO-ATP2d | 2d | 28 ± 8 | 0.82 ± 0.09 | | | |
| 8-bromo-ATP | | 22 ± 5 | 0.63 ± 0.04 | | | |
| 8-ethylS-ATP | 6c | 12 ± 5 | 0.30 ± 0.03 | | | |
| 8-BuNH-ATP | 7 | 20 ± 7 | 0.28 ± 0.03 | | | |
| 8-BuO-ATP | 8 | 26 ± 5 | 0.20 ± 0.01 | | | |

FIG. 4

C8-SUBSTITUTED PURINE NUCLEOTIDE ANALOGS

FIELD OF THE INVENTION

The present invention relates to C8-substituted purine nucleotide analogs and their use as inhibitors of nucleoside triphosphate diphosphohydrolases (NTPDases), and is particularly concerned with such compounds which provide effective and specific inhibition of NTPDases.

BACKGROUND OF THE INVENTION

In 1971, results of extensive studies on neurotransmission, which was resistant to conventional adrenergic and cholinergic antagonists, led Burnstock to propose that the purine nucleotide ATP and/or the purine nucleoside adenosine, released at synaptic junctions, might mediate a non-adrenergic, non-cholinergic signalling (1–7). Burnstock also hypothesized that nerves released purines which interact on their target cells with purinergic receptors (or purinoceptors) for either ATP, or its breakdown product adenosine (8, 9). The putative ATP-selective receptors were termed $P_2$-purinoceptors, whereas the adenosine receptors, were termed $P_1$-purinoceptors (10). Soon, purinoceptors were identified, characterized, and localized in a variety of systems, organs, cells and cell extracts. At the beginning, purinoceptors were classified according to their pharmacological and physiological properties, but with the advent of molecular biology tools, genes encoding purinoreceptors were cloned and a new classification emerged (see 11 for a complete review). Extracellular ATP and ADP and its metabolite adenosine exert multiple effects through these purinoceptors. In the cardiovascular system, these compounds influence platelet aggregation, vascular tone, heart function and recruitment of blood cells involved in inflammatory processes (12–15). In the digestive system, it affects electrolyte secretion, gastrointestinal motility, stomach acid secretion and other secretions coming from accessory glands: parotid, liver and exocrine pancreas (16–20). Presence of purinoceptors in the immune system also support a role of extracellular purines and pyrimidines in the immune response (11, 21–25). Presence of these receptors in the central and peripheral nervous systems also supports a role in neurotransmission for these compounds (26–29). These localizations combined with the effects induced by the administration of nucleotides confirm the functions of these nucleotides and their metabolites.

A fundamental question is what determines extracellular concentrations of nucleosides and nucleotides in the extracellular compartment. Basically, these are five parameters involved: 1-Rate of release from the source (cell); 2-Rate of diffusion and size of the extracellular compartment; 3-Metabolism by ectonucleotidases; 4-Binding to proteins on the cell surface; and 5-Uptake by the cells (translocation or endocytosis). Ectoenzymes with ectonucleotidase activities often localized in proximity of the target cells are believed to play key roles as modulators of the purine or pyrimidine actions. Among the ectoenzymes which display ectonucleotidase activities, one finds alkaline phosphatase [EC 3.6.1.3] which is widely distributed in the different systems of the body, protein kinase reported in certain cell types, ecto-nucleotide pyrophosphatase/phosphohydrolase [EC n.d.] which converts nucleoside triphosphate into nucleoside monophosphate and 5'-nucleotidase [EC 3.1.3.5] which convert nucleoside monophosphate into nucleoside (30–34).

Ectonucleotidases, often located on the target cells, rapidly dephosphorylate the nucleotide into the corresponding nucleoside thereby ending the $P_2$ stimulation and thereby inducing a $P_1$ type stimulation (31, 33, 36). Quite often, the physiological response elicited by the nucleoside antagonizes the action induced by the corresponding nucleotide (adenosine vs ATP) (14–15). Adenosine is generally considered as a negative feedback modulator (retaliatory metabolite) of cell and organ energy demand and consumption. It interacts with $P_1$ purinoceptors which comprise at least four subtypes $A_1$, $A_{2A}$, $A_{2B}$ and $A_3$, first classified into those that inhibit ($A_1$) and those that stimulate adenylate cyclase ($A_2$) (11). They were later classified according to their pharmacological properties and they are now distinguished by their amino-acid sequences (11).

Once released, nucleotides and nucleosides diffuse in the extracellular space and reach their receptor on target cells. Many enzymes contribute to the extracellular metabolism of nucleotides including alkaline phosphatase, ectokinases and deaminases. Perhaps the most important ones are those that convert nucleotides and nucleosides. Many reports have described ecto-ATPase, ecto-ADPase, and ecto-5'-nucleotidase activities in a variety of tissues and cells. The latter was purified, characterized biochemically, and its encoding gene was defined (34). As for the conversion of ATP to ADP and AMP, up until recently, it was believed that two distinct ecto-enzymes were involved in the conversion of ATP to ADP, and ADP to AMP, i.e., ecto-ATPase and ecto-ADPase, respectively (30). The detection of the NTPDase at the surface of vascular cells has presented another alternative for the conversion of ATP to AMP at the cell surface (37). The identification of a mammalian ATP diphosphohydrolase or apyrase goes back to the early 1980s when LeBel et al. described an enzyme that could sequentially catalyse the hydrolysis of γ and β phosphate residues of triphospho- and diphosphonucleosides (38). In a series of studies, the enzyme was purified, characterized, and identified as an ectoenzyme (39). A second isoform was identified, purified, and characterized in the bovine aorta (40) and placenta (41). Recent reports describing the homology between potato apyrase and human CD39, showing a comparison of bovine and porcine ATPDases, and the cloning and sequencing of the human ATPDase cDNA and reexpression of the human protein in COS cells, led to the demonstration that ATPDase isoform II and CD39 were the same protein (42–44).

Among many reported inhibitors of NTPDases, one finds analogs of purines, heavy metals, such as $Cd^{2+}$ and $Hg^{2+}$ (44, 46) and molecules belonging to the suramin family, Evans blue and also other types of molecules.

Purine analogs, such as β, γ-MetATP, β, γ-imido-ATP and ADPβS, may be used to inhibit the NTPDase (47). These analogs share a common characteristic, that is they all bear a substituted group on the phosphate chain. Moreover, all these analogs are purinoceptor ligands. Other nucleotide analogs have also been reported as NTPDase inhibitors, mainly ARL67156 and PPADS. These analogs have been reported to inhibit ecto-ATPase activity (48–51). Finally, two other purine analogs have been reported as NTPDase inhibitors: fluorosulfonylbenzoyl adenosine (FSBA) and 2-thioether-AMP-S (46, 52). However, contrary to purine analogs, FSBA causes an irreversible NTPDase inhibition.

Many P2 antagonists related to suramin (53), reactive blue (54), reactive red (55), Evans blue (56), trypan blue (56) and small aromatic isothiocyanoto-sulphonates (57), have been reported to be ecto-nucleotidase inhibitors. Other molecules have been proposed as non-specific NTPDase inhibitors, such as sodium azide, sodium fluoride (46) and 9-amino-1,2,3,4-tetrahydroacridine or THA (58).

Based on the facts that (a) NTPDases play a major role in the regulation of purine nucleotide and nucleoside levels and (b) purine nucleotides and nucleosides are involved in and influence a number of biological processes, modulation of the activity of NTPDases may have significant effects on such biological processes. Therefore, there exists a need for effective inhibitors of NTPDases, to better modulate the activity of NTPDases, thus modulating the levels of purine nucleotides and nucleosides, which in turn results in the modulation of a variety of biological processes.

SUMMARY OF THE INVENTION

An aspect of the present invention is a C8-substituted purine nucleotide analog, wherein the analog is substituted at the C8 position with a substituent other than H.

A further aspect of the present invention is a composition comprising the above-mentioned analog in admixture with a suitable diluent or carrier.

Yet a further aspect of the present invention is a method for modulating the activity of an NTPDase enzyme comprising exposing the enzyme to the above-mentioned analog or composition.

In a preferred embodiment, the present invention provides a method for inhibiting the activity of an NTPDase enzyme comprising exposing the enzyme to the above-mentioned analog or composition.

Yet a further aspect of the present invention is a method for modulating the level of purine nucleotide(s) and/or nucleoside(s) and/or metabolite(s) or derivative(s) thereof in a biological system, comprising the step of introducing into said system the above-mentioned analog or composition.

Yet a further aspect of the present invention is a method for modulating the activity of a biological process in a biological system, wherein said process is affected by the level of purine nucleotide(s) and/or nucleoside(s) and/or metabolite(s) or derivative(s) thereof in said system, comprising the step of introducing into said system the above-mentioned analog or composition.

Yet a further aspect of the present invention is a use of the above-mentioned analog or composition for modulating the level of purine nucleotide(s) and/or nucleoside(s) and/or metabolite(s) or derivative(s) thereof in a biological system.

Yet a further aspect of the present invention is a use of the above-mentioned analog or composition for modulating the activity of a biological process in a biological system, wherein said process is affected by the level of purine nucleotide(s) and/or nucleoside(s) and/or metabolite(s) or derivative(s) thereof in said system.

Yet a further aspect of the present invention is a commercial package containing the above-mentioned analog or composition together with instructions for modulating the level of purine nucleotide(s) and/or nucleoside(s) and/or metabolite(s) or derivative(s) thereof in a biological system.

Yet a further aspect of the present invention is a commercial package containing the above-mentioned analog or composition together with instructions for modulating the activity of a biological process in a biological system, wherein said process is affected by the level of purine nucleotide(s) and/or nucleoside(s) and/or metabolite(s) or derivative(s) thereof in said system.

BRIEF DESCRIPTION OF THE DRAWINGS

FIG. 4: Kinetic parameters of bovine spleen NPTase for ATP, ADP and purine analogs. Experiments were carried out in triplicate and results are expressed as the mean±SEM of the best fit obtained with GraFit 4 software (Erithacus, UK). Apparent Km and Vmax were estimated from Eadie and Hofstee representation and Ki's from Dixon plots.

A) Effect of 8-BuS-ATP (0.1–1000 pmol) on denuded mesenteric bed of guinea pig. Results are expressed as % of control (control=37 mm Hg). No variations of perfusion pressure were measured. Results are the mean±SEM of at least three experiments.

B) Effect of 8-BuS-ATP on the relaxing effect of ATP on intact mesenteric bed. ATP (0.1–10000 pmol) in the presence of 7 $\mu$M of 8-BuS-ATP (open bars) or in absence (control: closed bars). Results are expressed as % of vasodilation measured from a precontracted vessel (200 $\mu$M of noradrenaline). No significant difference was observed. Results are the mean±SEM of at least three experiments.

C) Vascular responses with or without endothelium. Endothelium integrity was tested with 100 pmol of NK-1 (closed bar) and blood vessel responsiveness was evaluated by 3 nmol of NaNP (open bar). Results are expressed as % of vasodilation measured from a precontracted vessels (200

μM of noradrenaline). In denuded mesentery there is significant response to NK-1. Results are the mean of three experiments or more.

DESCRIPTION OF THE EMBODIMENTS OF THE INVENTION

The present invention provides C8-substituted purine nucleotide analogs. In a preferred embodiment, such analogs are ATP analogs, examples of which the Applicant has prepared and characterized. Such analogs have a variety of uses, a preferred one of which is the inhibition of NTPDases, which the Applicant has characterized. For this use, the compounds of the invention were found to be effective.

Figure 1A:
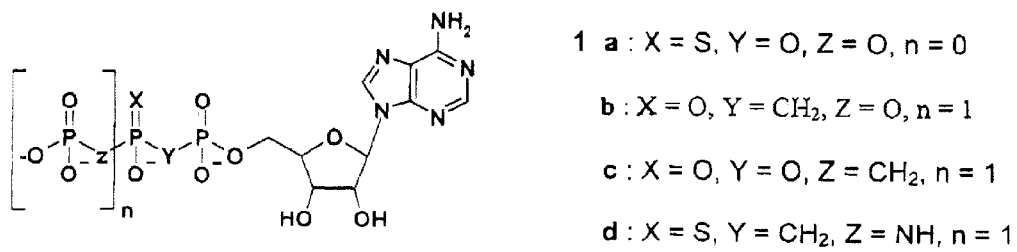
FIG. 1: Structures of different ATP analogs.
Figure 1B:
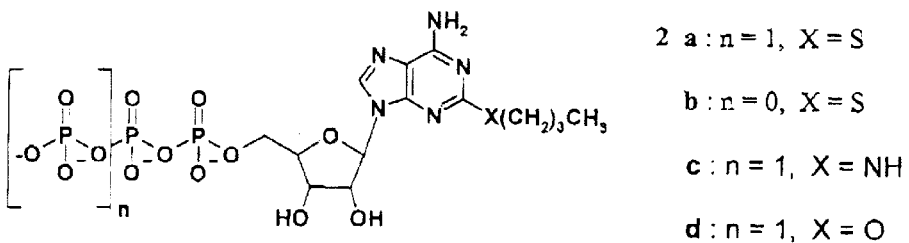
Figure 1C:
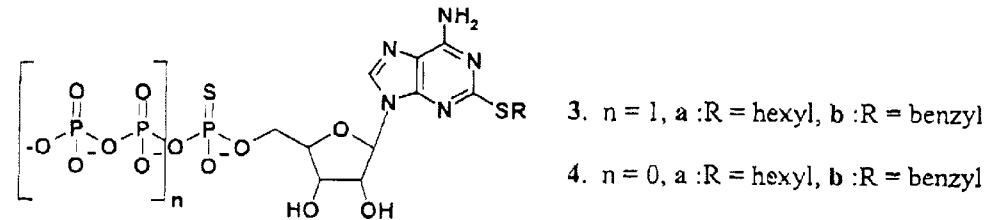
Figure 1D:
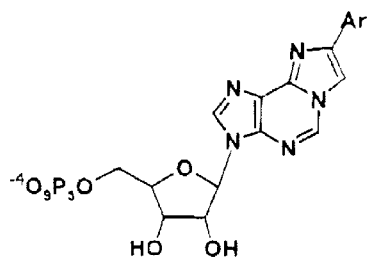
Figure 1E:
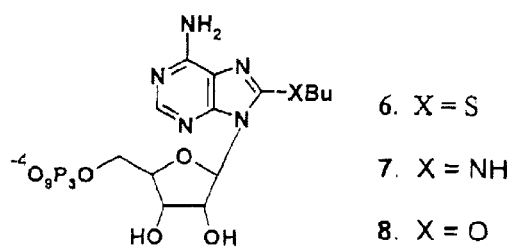
Figure 2:
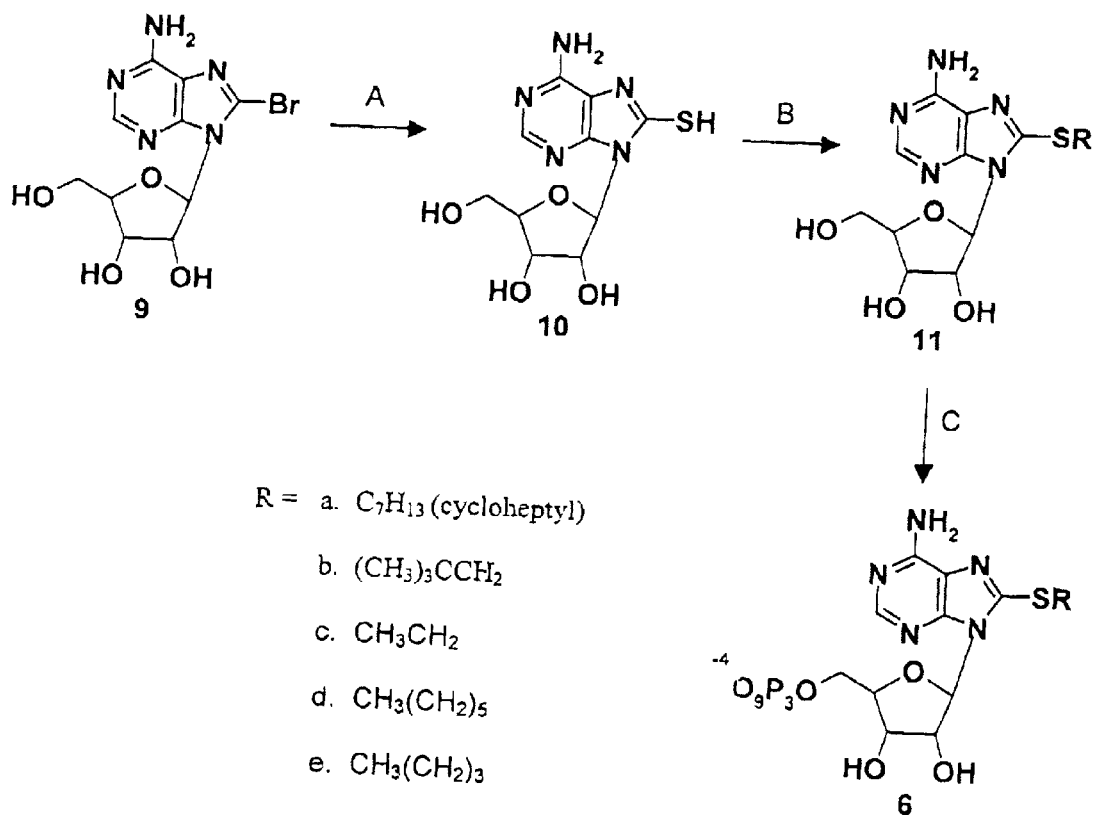
FIG. 2: Scheme of synthesis of 8-thioether-ATP derivatives. A. 10 eq. NaSH/wet DMF/100° C./overnight/100% yield. B. 1. compound 10/MeOH/0.25 M NaOH/RT, freeze drying. 2. alkyl bromide/DMF/60° C./overnight/83–93% yield. C. 1. $POCl_3$/proton sponge. 2. $P_2O_7H_2(Bu_3NH^+)_2$. 3. 0.2 M TEAB.

The Applicant has selected and synthesized purine nucleotide analogs, more particularly ATP analogs, specifically compounds 2a–d and 6–8 (illustrated in FIGS. 1 and 2). Based on the promising hydrolytic stability of compounds 6–8, the Applicant has synthesized a new series of 8-thioether ATP analogs, i.e., compounds 6a–e, and has evaluated their use as NTPDase inhibitors. In view of finding a specific and potent NTPDase inhibitor, the Applicant has examined two series of ATP analogs substituted at positions C2 and C8, respectively.

As described in the Examples below, this evaluation revealed that at least one of the compounds tested was improved with respect to, for example, at least one criterion selected from the following:
1. Resistance to NTDPase hydrolysis.
2. Potency as an NTDPase inhibitor.
3. Nature of the inhibition.
4. Ki value.
5. Effects on P2 (e.g. P2X and P2Y) purinergic receptors.

Via the above evaluation, the Applicant has first demonstrated that analogs substituted with electron donating groups at C8 were more resistant to NTPDase hydrolysis than the corresponding C2 substituted analogs. Therefore, an aspect of the invention are C8-substituted purine nucleotide analogs, a preferred embodiment of the invention being ATP analogs.

The C8-substituted purine nucleotide analogs of the invention may be substituted at this position, for example, by electron donating groups. Such groups include but are not limited to ethers, thioethers and amines. Examples of ethers, thioethers and amines that are aspects of the invention are those with, for example, alkyl groups. Such alkyl groups may be, for example, cyclic-, branched- and/or n-alkyl groups. An example of a preferred cyclic alkyl group according to the invention is the cycloheptyl ($C_7H_{13}$) group. An example of a preferred branched alkyl group according to the invention is the 2,2-dimethyl-propyl (($CH_3)_3CCH_2$) group. Examples of preferred n-alkyl groups according to the invention are those up to 6 carbons in length. A particularly preferred embodiment is an n-butyl ($CH_3(CH_2)_3$) group.

The Applicant has further demonstrated that of the C8-substituted ATP analogs analyzed, all of which were found to possess a degree of resistance to NTPDase hydrolysis, compounds 6a, 6b, 6d and 6e were more resistant to hydrolysis by NTPDase than compounds 7, 8 and 6c. The Applicant has further evaluated the C8-substituted ATP analogs compounds 6a, 6b, 6d and 6e of the invention for their potency as NTPDase inhibitors, and has demonstrated that all four of these compounds are good inhibitors. Therefore, compounds 6a, 6b, 6d and 6e are further preferred aspects of the present invention.

Of all the compounds tested, compound 6e was found to be most resistant to hydrolysis by NTPDase, and was further found to exhibit competitive inhibition with a Ki value lower than those measured for compounds 6a, 6b and 6d. Therefore, as noted above, the Applicant notes that compounds 6a, 6b, 6d and 6e are further preferred aspects of the present invention, and compound 6e represents a particularly preferred aspect of the invention.

The Applicant has further evaluated compound 6e of the invention with respect to any effects on purinoceptors, and found that this compound does not interact with either P2X- or P2Y-purinoceptors. Therefore, the compounds of the invention act as, for example, effective and specific inhibitors of NTPDase.

Therefore, the invention provides C8-substituted purine nucleotide analogs, which may, for example, be used for the modulation of NTPDase activity. In a preferred embodiment, the C8-substituted purine nucleotide analogs of the invention may be used for the inhibition of NTPDase activity. Given the wide variety of biological processes which are affected by the purine nucleotides and/or nucleosides and/or their metabolites and/or derivatives, the compounds of the invention may be utilized to alter the activity of such processes via the alteration of the levels of purine nucleotides and/or nucleosides and/or their metabolites and/or derivatives.

Accordingly, an aspect of the present invention is a method to alter or modulate the level of purine nucleotides and/or nucleosides and/or their metabolites and/or derivatives in a biological system. A further aspect of the present invention is a method of altering the activity of a biological process which is affected by the levels of purine nucleotides and/or nucleosides and/or their metabolites and/or derivatives in a biological system. The modulation of such processes occurs by, for example, the action of purine nucleotides and/or nucleosides and/or their metabolites and/or derivatives on cell surface receptors, such as purinoceptors. Such cell surface receptors can act to modulate a large number of biological processes using a variety of mechanisms. Examples of such mechanisms include acting through G-proteins to generate a variety of signalling cascades (e.g., involving inositol phospholipid or other messengers and/or the mobilization of calcium stores), the activation of ligand-gated ion channels, the inducation of channels and/or pores, and the modulation of ion fluxes and other responses.

The processes noted above which may be modulated as a result of the modulation of the levels of purine nucleotides and/or nucleosides and/or their metabolites and/or derivatives include, but are not limited to, the following:
1. In the cardiovascular system, such processes include, for example, platelet aggregation; modulation of vascular tone and function (e.g., vasoconstriction and vasodilation) and blood flow; heart function and performance; and the recruitment and adhesion of blood cells involved in inflammatory processes.
2. In the nervous system (central and peripheral), such processes include, for example, neurotransmission.
3. In sensory systems, such processes include, for example, activity of sensory organs and/or cells.
4. In muscle tissues, such processes include, for example, activity (e.g., contractile responses) of visceral smooth muscle and skeletal muscle.
5. In the pulmonary system, such processes include, for example, secretion by cells of the pulmonary system.
6. In the immune system, such processes include, for example, function of various immune cell types, and the modulation of diverse responses of the immune system.

7. In endocrine, neurocrine and exocrine systems, such processes include, for example, secretion of a variety of compounds from a variety of cell types in these systems. Such cell types include, for example, those present in the pancreas, and parotid, lacrimal, thyroid, adrenal and pituitary glands.
8. In paracrine cells, such as platelet and mast cells, such processes include, for example, secretion of compounds from these cells. Further, as noted above, the processes affected also include platelet aggregation, and thrombus formation, as well as the additional recruitment of new platelets to the developing thrombus.
9. In the reproductive system and cells of the reproductive system, such processes include, for example, contraction of smooth muscle tissue (e.g., myometrium) and activity of germ cells.
10. In hepatic tissue, such processes include, for example, hepatic tissue function and the biochemical and biological processes which occur therein (e.g. gluconeogenesis and glycogenolysis), as well as the secretion of compounds (e.g., thromboxanes and prostaglandins) from hepatic cells and tissue.
11. In renal and gastrointestinal tissues, such processes include, for example, secretion (e.g., of electrolyte(s) and stocmach acid) from such tissues and cells therein, and gastrointestinal motility.
12. In connective tissue, skin and bone, such processes include, for example, the modulation of a variety of activities and functions within these tissues and cells therein, such as growth and differentiation.
13. In tumor cells, such processes include, for example, a variety of activities and functions, such as growth regulation. Therefore, the growth of tumor or cancer cells and tissue may be modulated, and thus the invention further provides compounds, compositions, methods, uses, and commercial packages for the treatment of cancer.

Therefore, the invention provides compounds, compositions, methods, uses, and commercial packages for the modulation of activities and function in the cardiovascular, nervous, immune, inflammatory, sensory and reproductive systems; in muscle, endocrine, neuroendocrine, exocrine, paracrine, germ, hepatic, renal and gastrointestinal cells and tissues; as well as in connective tissue, skin and bone. The invention further provides compounds, compositions, methods, uses, and commercial packages for the modulation of a process such as aggregation and thrombogenicity. In an embodiment, such modulation comprises an increase in aggregation and thrombogenicity.

Yet a further aspect of the present invention is the use of a compound of the invention for, for example, the methods and purposes described above.

The compounds of the present invention may also be adapted for certain applications using methods known in the art. For example, a compound of the invention may be attached to a solid phase or matrix. In this form, the compound may be utilized for the isolation and purification of species with which it binds/interacts, for example, using the technique of affinity chromatography. Such species comprise proteins which bind purine nucleotides and/or their metabolites and/or derivatives, an example of such a protein being an NTPDase enzyme. In other embodiments, the compounds of the invention may be modified for their use in a variety of methods such as diagnostic methods.

The compounds of the invention or corresponding modified versions may be a component of an appropriate composition of the invention, comprising a compound of the invention or a corresponding modified version and a suitable diluent or carrier. Such compositions may be, for example, utilized in the uses and methods described above. Such compositions include pharmaceutical compositions, comprising a compound of the invention or a corresponding modified version and a suitable pharmaceutically acceptable diluent or carrier. The compounds, corresponding modified versions, or the compositions of the invention may also be a component of a commercial package of the invention, which comprises a compound or composition of the invention together with instructions for, for example, the uses and methods described above.

The following examples are provided in order to illustrate the embodiments of the present invention and are not meant to limit the scope of the invention.

EXAMPLE 1

Synthesis, Purification and Characterization of ATP Analogs

General methods. New compounds were characterized by proton and carbon nuclear magnetic resonance using a Bruker AC-200 or DPX-300 spectrometer. The chemical shifts are reported in ppm relative to TMS as an internal standard. Nucleotides were characterized also by $^{31}$P-NMR in $D_2O$ using 85% $H_3PO_4$ as an external reference on a Bruker AC-200 spectrometer. Mass spectra were recorded on an AutoSpec-E-FISION VG high resolution Mass Spectrometer. Nucleotides were characterized by FAB (fast atom bombardment) and high resolution FAB using a glycerol matrix under FAB negative conditions on AutoSpec-E-FISION VG high resolution Mass Spectrometer. Separation of the newly synthesized nucleotides was achieved using LC (Isco UA-6) using DEAE A-25 Sephadex ($HCC_3^-$ form) anion exchanger as described below. Final purification was done using an HPLC (Merck-Hitachi) system using a semi-preparative LiChroCART LiChrospher 60 RP-select B column (1×25 cm, Merck KgaA) and a linear gradient of 0.1 M triethylammonium acetate buffer (TEAA, pH 7.5) and methanol (see below) at 6 mL/min flow rate. For analytical purposes, a LiChroCART LiChrospher 60 RP-select B column (250 mm×4.6 mm, Merck KGaA) was used applying the same gradient as above at 1 mL/min flow rate. The purity of the nucleotides described below as evaluated on an analytical column in two different solvent systems. One solvent system (I) was 0.1 TEAA/$CH_3OH$, 80:20 to 20:80 in 20 min. The second solvent system (II) was (A) 5 mM tetrabutylammonium phosphate (TBAP) in methanol and (B) 60 mM ammonium phosphate and 5 mM TBAP in 90% water/10% methanol, applying a gradient of 25% A to 75% A in 20 min.

The selection and synthesis of ATP analogs, compounds 2a–d and 6–8 (FIGS. 1 and 2), for their evaluation as NTPDase inhibitors were based on the promising hydrolytic stability of compounsd 6–8. The desired derivatives, 6a–e, were obtained in three steps from 8-Br-adenosine in good yields (FIG. 2). 8-Mercapto-adenosine, 10, was obtained in a quantitative yield from 8-Br-adenosine upon treatment with 10 eq of NaSH in wet DMF at 100° C. overnight. The corresponding dry sodium thiolate salt, obtained upon dissolution of 10 in MeOH/0.25 M NaOH and subsequent freeze drying, was treated with the appropriate alkyl bromide in DMF at 60° C. to yield compounds 11 in high yields. Finally these compounds were 5'-triphosphorylated, to give nucleotides 6 in reaonsable yields (64). Compound 6 of FIG. 1E and compound 6e of FIG. 2 are one in the same, i.e., with a thiobutyl ($CH_3(CH_2)_3S$) group as the C8 substituent. This compound was prepared as described previously (64).

8-Mercaptoadenosine (10). NaSH (0.8 g, 10 eq) was added to a solution of 8-bromoadenosine (0.5 g, 1.44 mmol) in DMF (7 mL). The mixture was warmed to 100° C. and a few drops of water were added to improve solubility. The mixture was stirred at 100° C. overnight. The solvent was evaporated under high vacuum and the residue was coevaporated repeatedly with MeOH, until the residue turned into a solid. The residue was dissolved in water and neutalized with NaOH. After freeze drying, the product was purified on a silica gel column ($CHCl_3$:MeOH 10:1). The product was obtained as a yellowish powder (100% yield, mp 169–170° C.). $^1$H-NMR ($CD_3OD$, 200 MHz) 8.09 (s, 1H, H-2), 6.65 (d, J=7 Hz, 1H, H-1'), 5.01 (dd, J=7, 5.5 Hz, 1H, H-2'), 4.39 (dd, J=5.5, 2.5 Hz, 1H, H-3'), 4.13 (q, J=2.5 Hz, 1H, H-4'), 3.87 (dd, J=12.5, 2.5 Hz, 1H, H-5'), 3.71 (dd, J=1.25, 3 Hz, 1H, H-5'); $^{13}$C-NMR ($CD_3OD$, 300 MHz) δ 167.88 (C-6), 151.92 (C-2), 148.12 (C-4), 147.88 (C-8), 107.00 (C-5), 88.62 (C-1'), 85.59 (C-4'), 70.70 (C-2'), 70.62 (C-3'), 62.13 (C-5'); MS ($CI/NH_3$): m/z 317 $M+NH_4^+$.

8-(Thiocycloheptyl) adenosine (11a). A suspension of 8-merceptoadenosine (75 mg, 0.25 mmol) in MeOH (2 mL) was dissolved in 0.25 M NaOH (1 mL). The clear, yellow solution was stirred at room temperature for 1 h. After freeze drying, the thiolate sodium salt obtained as a yellowish solid, was dissolved in dry DMF (2 mL) and bromocycloheptane (38 μL, 1.1 eq) was added. The solution was stirred overnight under nitrogen at 60° C. The solvent was evaporated under high vacuum and the yellow residue was coevaporated repeatedly with MeOH, until the residue turned into a yellow solid. The solid was triturated with petroleumether/ether 1:1, and then separated on a silica gel column ($CHCl_3$:MeOH20:1). Product 11a was obtained as a white solid in 83% yield (82 mg) after evaporation and drying, mp 205–6° C. $^1$H-NMR (DMSO-$d_6$, 200 MHz): 8.07 (s, 1H, H-2), 7.36 (br.s, 2H, $NH_2$), 5.84 (d, J=7 Hz, 1H, H-1'), 5.00 (dd, J=7, 5 Hz, 1H, H-2'), 4.16 (dd, J=5, 2 Hz, 1H, H-3'), 4.07–3.91 (m, 2H, H-4' & SCH), 3.68 (dd, J=12, 4 Hz, 1H, H-5'), 3.52 (dd, J=1.25, 4 Hz, 1H, H-5'), 2.19–1.93 (m, 2H), 1.84–1.42 (m, 11H); $^{13}$C-NMR (DMSO-$d_6$, 300 MHz): δ 154.80 (C-6), 151.51 (C-2), 150.03 (C-4), 147.94 (C-8), 119.75 (C-5), 88.96 (C-1'), 86.64 (C-4'), 71.31 (C-2'), 71.08 (C-3'), 62.27 (C-5'), 48.42 (SCH), 34.51 ($CH_2$), 34.14 ($CH_2$), 27.77 ($CH_2$), 27.76 ($CH_2$), 25.14 ($CH_2$), 25.04 ($CH_2$). FAB(positive): m/z 396 $MH^+$.

8-(Thio-2,2-dimethyl-propyl)-adenosine (11b). The compound was prepared as described for 8-(thiocycloheptyl)-adenosine and obtained in 79% yield (73 mg) as a yellowish solid, mp 141–2° C. $^1$H-NMR ($CD_3OD$, 200 MHz) δ 8.06 (s, 1H, H-2), 6.02 (d, J=7 Hz, 1H, H-1'), 4.99 (dd, J=7, 5 Hz, 1H, H-2'), 4.33 (dd, J=5, 2 Hz, 1H, H-3'), 4.17 ("q", J=2 Hz, 1H, H-4'), 3.88 (dd, J=12.5, 2.5 Hz, 1H, H-5'), 3.72 (dd, J=12.5, 3 Hz, 1H, H-5'), 3.42 and 3.35 (AB, J=7 Hz, 2H, SCH), 1.09 (s, 9H, $SCH_2(CH_3)_3$); $^{13}$C-NMR ($CD_3OD$, 300 MHz) 155.92 (C-6), 152.91 (C-4), 152.11 (C-2), 151.69 (C-8), 110.64 (C-5), 91.19 (C-1'), 88.89 (C-4'), 74.13 (C-2'), 73.20 (C-3'), 64.17 (C-5'), 47.69 ($SCH_2$), 29.07 (3C, $SCH_2(CH_3)_3$); MS ($CI/NH_3$) m/z: 368 $(M-H)^+$.

8-(Thioethyl)-adenosine (11c). A suspension of 8-mercaptodenosine (270 mg, 0.9 mmol, in 7 mL MeOH) was dissolved in 0.25 M NaOH (3.6 mL). The clear, yellow solution was stirred at room temperature for 1 h. After freeze drying, the thiolate sodium salt, obtained as a yellowish solid, was dissolved in dry DMF (3 mL) and bromoethane (101 μL, 1.5 eq) was added. The solution was stirred under nitrogen at room temperature for 3 h. The solvent was evaporated under high vacuum and the yellow residue was coevaporated repeatedly with MeOH, until the residue turned into a yellow solid. The solid was separated on a silica gel column ($CHCl_3$:MeOH 15:1). Product 11c was obtained as a white solid in 93% yield after evaporation and drying (273 mg), mp 176° C. $^1$H-NMR (CMSO-$d_6$, 200 MHz): 8.05 (s, 1H, H-2), 7.31 (br. s, 2H, $NH_2$), 5.76 (d, J=7 Hz, 1H, H-1'), 5.66 (dd, J=8.5, 3.5 Hz, 1H, OH-5'), 5.42 (d, J=6 Hz, 1H, OH-2'), 5.21 (d, J=4 Hz, 1H, OH-3'), 4.99 (br. q, J=6 Hz, 1H, H-2'), 4.15 (bs, 1H, H-3'), 3.96 (br. s, 1H, H-4'), 3.68 (dt, J=12, 3.5 Hz, 1H, H-5'), 3.60–3.44 (m, 1H, H-5'), 3.43–3.14 (m, 1H, $SCH_2CH_3$), 1.36 (t, J=7 Hz, 3H, $SCH_2CH_3$); $^{13}$C-NMR (DMSO-$d_6$, 300 MHz): 154.49 (C-6), 151.30 (C-2), 150.40 (C-4), 148.53 (C-8), 119.66 (C-5), 88.86 (C-1'), 86.63 (C-4'), 71.29 (C-2'), 70.01 (C-3'), 62.24 (C-5'), 26.77 ($SCH_2CH_3$), 14.85 ($SCH_2CH_3$); MS ($CI/CH_4$): m/z 328 $MH^+$; High resolution MS: calcd for $C_{12}H_{18}N_5O_4S$ 328.1079, Found 328.1069.

8-(Thio-n-hexyl)-adenosine (11d). The compound was prepared as described for 8-(thioethyl)-adenosine and obtained in 91% yield (314 mg) as a white solid, mp 169–171° C. $^1$H-NMR (DMSO-$d_6$, 200 MHz): δ 8.05 (s, 1H, H-2), 7.29 (br.s, 2H, $NH_2$), 5.77 (d, J=7 Hz, 1H, H-1'), 5.67 (dd, J=9, 3.5 Hz, 1H, OH-5'), 5.42 (d, J=6 Hz, 1H, OH-2'), 5.21 (d, J=4 Hz, 1H, OH-3'), 4.99 ("q", J=6 Hz, 1H, H-2'), 4.15 (br.s, 1H, H-3'), 3.96 (br.s, 1H, H-4'), 3.67 (dt, J=12, 3.5 Hz, 1H, H-5'), 3.60–3.43 (m, 1H, H-5'), 3.42–3.18 (m, 1H, $SCH_2$), 1.69 (quint, J=7 Hz, 2H, $SCH_2CH_2$), 1.50–1.18 (m, 6H, —$CH_2CH_2CH_2CH_3$), 0.86 (t, J=7 Hz, 3H, $CH_3$); $^{13}$C-NMR (DMSO-$d_6$, 300 MHz): 154.55 (C-6), 151.27 (C-2), 150.38 (C-4), 148.71 (C-8), 119.61 (C-5), 88.85 (C-1'), 86.63 (C-4'), 71.28 (C-2'), 71.02 (C-3'), 62.23 (C-5'), 32.37 ($SCH_2$), 30.70 ($CH_2$), 28.80 ($CH_2$), 27.71 ($CH_2$), 21.99 ($CH_2$), 13.88 ($CH_3$); MS ($CI/CH_4$): m/z 384 $MH^+$; High resolution MS: calcd for $C_{16}H_{26}N_5O_4S$ 384.1705, Found 384.1696.

Nucleoside 5'-Triphosphorylation. Nucleosides 11a–d were 5'-triphosphorylated according to a published procedure (60).

8-(Thiocycloheptyl)-adenosine 5'-triphosphate (6a). The compound was obtained in 60% yield (79 mg). Final separation was achieved on HPLC applying a linear gradient of TEAA/$CH_3OH$ 70:30 to 20:80 in 20 min (6 mL/min). $t_R$ 9.53 min. $^1$H-NMR ($D_2O$, 200 MHz): δ 8.17 (s, 1H, H-2), 6.09 (d, J=6 Hz, 1H, H-1'), 5.15 (t, J=6 Hz, 1H, H-2'), 4.62–4.51 (m, 1H, H-3'), 4.37–4.14 (m, 3H, H-4' & H-5'), 3.93–3 75 (m, 1H, SCH), 2.15–1.90 (m, 2H), 1.80–1.36 (m, 11H); $^{31}$P-NMR ($D_2O$, 200 MHz, pH 9) δ −5.34 (d), −10.37 (d), −21.32 (t); UV: λmax 282 nm. HRFAB: calcd for $C_{17}H_{27}N_5O_{13}P_3S$ 634.0539, Found 634.0540; $t_R$ 14.99 min (95% purity) using solvent system I, 13.19 min (97% purity) using solvent system II.

8-(Thio-2,2-dimethyl-propyl)-adenosine 5'-triphosphate (6b). The compound was obtained in 65% yield (77 mg). Final separation was achieved on HPLC applying a linear gradient of TEAA/$CH_3OH$ 70:30 to 20:80 in 20 min (6 mL/min). $t_R$ 7.51 min. $^1$H-NMR ($D_2O$, 200 MHz): δ 8.21 (s, 1H, H-2), 6.13 (d, J=6 Hz, 1H, H-1'), 5.20 (t, J=6 Hz, 1H, H-2'), 4.62 (dd, J=6 Hz, 1H, H-3'), 4.42–4.25 (m, 3H, H-4' & H-5'), 3.29 and 3.35 (ABq, J=12 Hz, 2H, $SCH_2$), 1.06 (s, 3H, $SCH_2(CH_3)_3$); $^{31}$P-NMR ($D_2O$, 200 MHz, pH 9) δ −10.23 (d), −10.79 (d), −22.61 (t); UV: λmax 282 nm. HRFAB: calcd for $C_{15}H_{25}N_5O_{13}P_3S$ 608.0382, Found 608.0360; $t_R$ 12.71 min (96% purity) using solvent system I, 11.31 min (95% purity) using solvent system II.

8-(Thioethyl)-adenosine 5'-triphosphate (6c). The compound was obtained in 43% yield (84 mg). Final separation was achieved on HPLC applying a linear gradient of TEAA/CH3OH 90:10 to 20:80 in 20 min (6 mL/min). $t_R$ 8.11 min. 1H-NMR (D2O, 200 MHz): 8.15 (s, 1H, H-2), 6.10 (d, J=6.5 Hz, 1H, H-1'), 5.17 (t, J=6.5 Hz, 1H, H-2'), 4.65–4.55 (m, 1H, H-3'), 4.40–4.16 (m, 3H, H-4' & H-5'), 3.30 and 3.26 (ABq of t, J=11.5, 7 Hz, 1H each, SCH2), 1.39 (t, J=7 Hz, 3H, CH3); 31P-NMR (D2O, 200 MHz, pH 9) −5.12 (d), −10.31 (d), −20.98 (t); UV: max 282 nm. HRFAB: calcd for C12H18N5O13NaP3S 587.9732, Found 587.9650; $t_R$ 7.16 min (96% purity) using solvent system I, 3.55 min (94% purity) using solvent system II.

8-(Thio-n-hexyl)-adenosine 5'-triphosphate (6d). The compound was obtained in 58% yield (111 mg). Final separation was achieved on HPLC applying a linear gradient of TEAA/CH3OH 70:30 to 20:80 in 20 min (6 mL/min). $t_R$ 10.73 min. 1H-NMR (D2O, 200 MHz): 8.17 (s, 1H, H-2), 6.01 (d, J=6.5 Hz, 1H, H-1'), 5.19 (t, J=6.5 Hz, 1H, H-2'), 4.64–4.55 (m, 1H, H-3'), 4.40–4.14 (m, 3H, H-4' & H-5'), 3.32 and 3.24 (ABq of t, J=14, 7 Hz, 1H each, SCH2), 1.73 ("quint", J=7 Hz, 2H, SCH2CH2), 1.52–1.09 (m, 6H), 0.82 (t, J=7 Hz, 3H, CH3); 31P-NMR (D2O, 200 MHz, pH 9) −5.12 (d), −10.25 (d), −21.03 (t); UV: max 282 nm; $t_R$ 15.25 min (>97% purity) using solvent system I, 15.52 min (>97% purity) using solvent system II.

EXAMPLE 2

Enzymology of Purine Nucleotide Analogs

The demonstration of the inhibitory properties of a given compound on a particular enzyme requires that a single site of catalysis is present in the medium. In other words, if a second enzyme competes for the substrate or generates the same reaction product it modifies the interpretation and would definitely rule out any conclusion about the inhibitor specificity. In the preparation used to demonstrate the inhibitory properties of C8-substituted ATP analogs, in this work, we previously showed that a single catalytic site was involved in the sequential hydrolysis of the gamma and beta phosphate residues of ATP (35).

Reagents and solutions. ATP, tetramisole, malachite green, bovine serum albumin fraction V (BSA), CHAPS, sodium nitroprussiate (NaNP), (−) arterenol bitartrate (noradrenaline), heparin and indomethacin were obtained from Sigma Chemical Co. (St-Louis, Mo., USA). ADP was obtained from Roche (Laval, QC., Canada), and Bradford reagent was purchased from Bio-Rad Laboratories (Mississauga, Ontario, Canada). [Star$^9$,Met(O$_2$)$^{11}$]SP (NK-1) was synthesized by Dr. W. Neugebauer from the Université de Sherbrooke. Preparation of Krebs and phosphate buffer saline (PBS) were as followed. Krebs solution: 5.5 mM glucose, 117.5 mM NaCl, 1.2 mM MgSO$_4$, 1.2 mM KH$_2$PO$_4$, 4.7 Mm KCl, 2.5 Mm CaCl$_3$, 25 Mm NaHCO$_3$, pH 7.4. PBS: 137 mM NaCl, 3 mM KCl, 10 mM Na$_2$HPO$_4$ and 1.7 mM KH$_2$PO$_4$, pH 7.4. All the other reagents were of analytical grade and obtained from Sigma Chemical Co. (St-Louis, Mo., USA).

Isolation of particulate fractions. Experiments were carried out with a particulate fraction obtained from bovine spleen according to the method of Sévigny et al. (37). Briefly, bovine spleens were cut in small pieces and homogenized (15–20%) with a Polytron in Tris-saline buffer supplemented with SBTI and PMSF as protease inhibitors. After filtration with cheesecloth and centrifugation at 600 g the supernatant is centrifuged at 22,000 g for 90 min, and the resulting pellet is suspended in bicarbonate buffer and loaded on a sucrose cushion (40%) and centrifuged for two hours at 100,000 g. The fraction floating on the cushion is harvested in five volumes of bicarbonate buffer. The pellet is suspended in Tris buffer/glycerol 7.5% and kept at −20° C.

NTPDase assays. Enzyme activity was routinely measured by the release of inorganic phosphorus with the malachite green colorimetric assay (61). Resistance to hydrolysis was measured at 37° C. in 1 ml of the following incubation medium: 8 mM CaCl$_2$, 5 mM tetramisole, 50 mM Tris base, 50 mM imidazole, buffered at pH 7.6, and 100 μM of either ATP or its analogs. Apparent $K_m$ and $V_{max}$ values for ATP, ADP and each of the hydrolysable purine nucleotide analogs were derived from Eadie and Hofstee plots, with substrate concentrations ranging between 10 and 300 μM for ATP and ADP, and between 15 and 100 μM for the analogs, unless stated otherwise. In both cases the reaction was started by the addition of 1.9 μg of the enzyme preparation and stopped after 7 min with 250 μL of the malachite green reagent. Apparent Ki values for non-hydrolysable purine nucleotide analogs were derived from Dixon replots, using inhibitor concentrations ranging from 0 to 100 μM. Reactions were performed in the same incubation buffer, as previously described and were started by the addition of non-saturating ATP concentrations. Protein concentration was determined with the Bradford microplate assay using bovine serum albumin as a standard of reference (62).

To reduce potential artifacts resulting from the solubilisation of NTPDase by detergents, a particulate fraction (prepared as described above) was used. It is important to mention that there was no other detectable level of ATPase or ADPase activity in the preparation, other than that attributable to NTPDase. Also, possible alkaline phosphatase activity was inhibited by tetramisole added to the assays. In view of finding a specific and potent NTPDase inhibitor, two series of ATP analogs were examined, which were substituted at positions C2 and C8, respectively.

Figure 3:
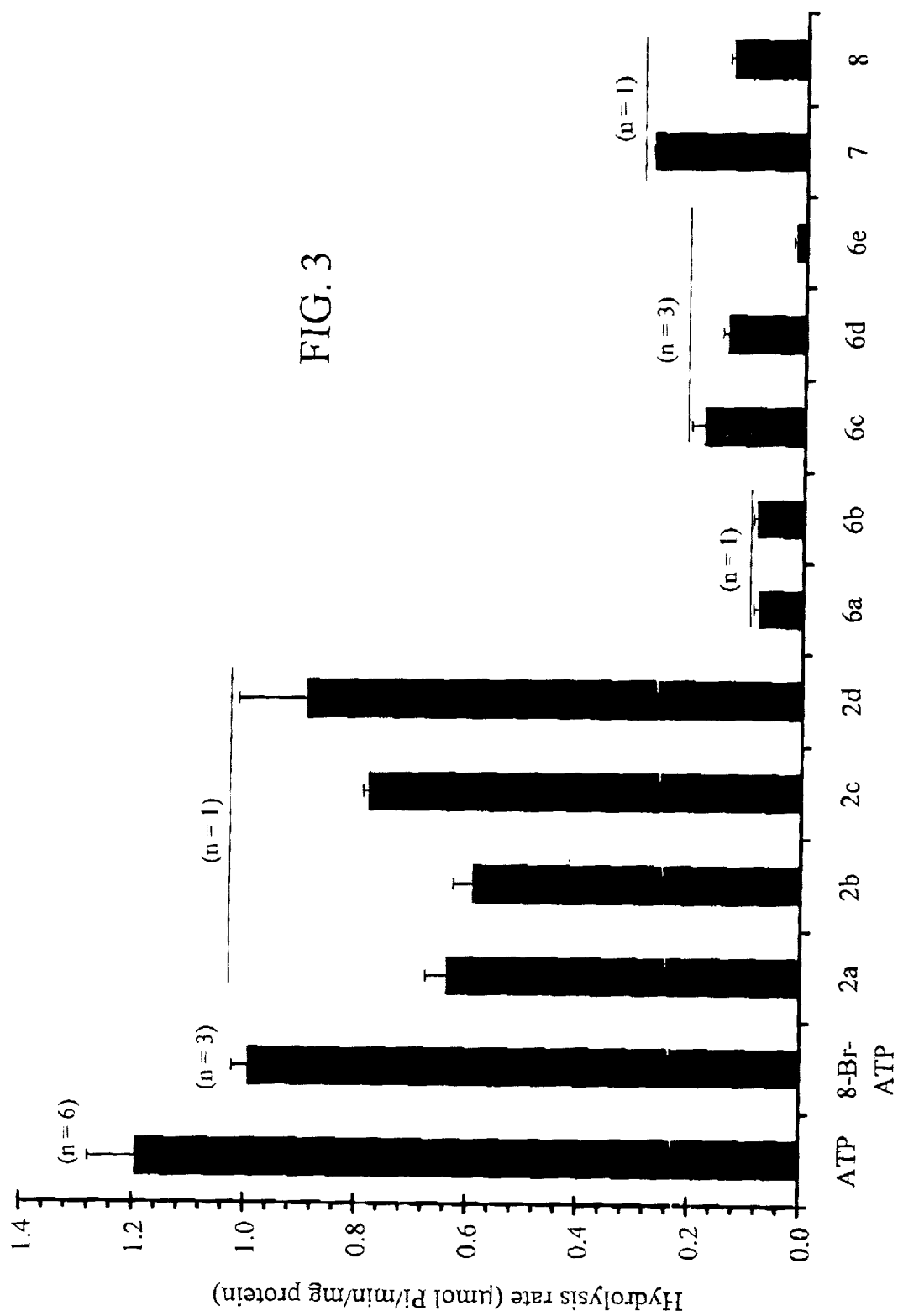
FIG. 3: Hydrolysis of ATP and analogs by NTPDase. ATP and analogs were used at a concentration of 100 $\mu$M. Hydrolysis was carried out at 37° C. for 7 min in the presence of 1.9 $\mu$g of protein. C2 substituted analogs (2a–d) are all hydrolyzed by the enzyme whereas C8-substituted analogs (6–8) are more or less resistant to NTPDase hydrolysis. Results are expressed as the mean±SEM of n replicate (see figure) carried out in triplicate.
Figure 5A:
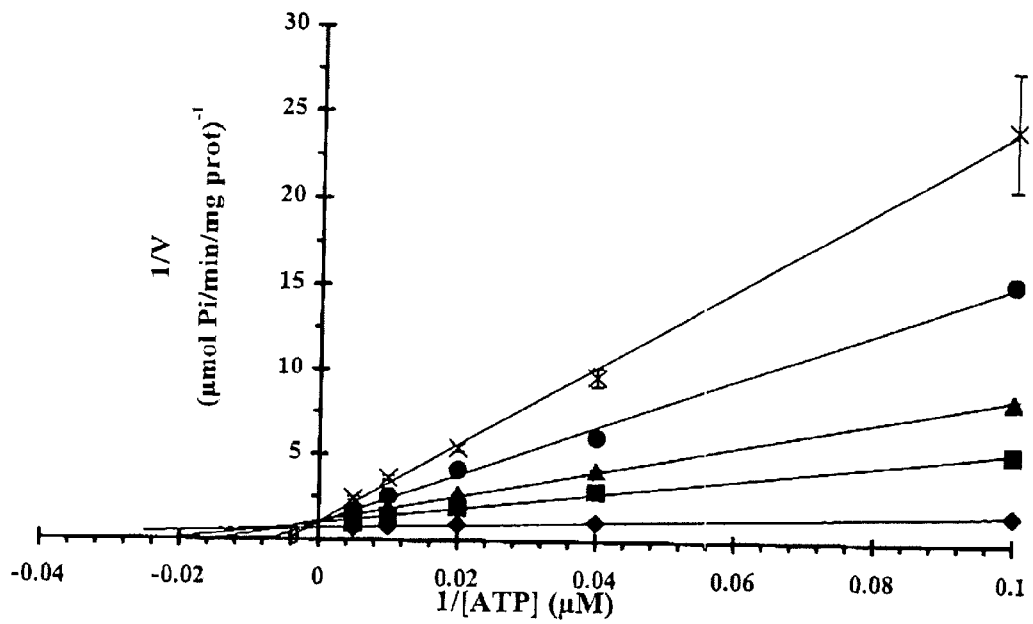
FIG. 5: Inhibitory effect of 8-BuS-ATP, 6e, on ATP hydrolysis by NTPDase. A) Lineweaver-Burk representation of NPTDase inhibition. ATP (10 to 100 $\mu$M) and 8-BuS-ATP: 0 $\mu$M: ♦; 10 $\mu$M: ■; 25 $\mu$M: ▲; 50 $\mu$M: ●; and 100 $\mu$M: X. B) Dixon plots of NTPDase inhibition. ATP as substrate: 10 $\mu$M (▲), 25 $\mu$M (■) and 50 $\mu$M (♦) and 8-BuS-ATP concentrations as above. 8-BuS-ATP produce a competitive inhibition with an estimated Ki of 10 $\mu$M. Results are expressed as the mean±SEM of two experiments each in duplicate.
Figure 5B:
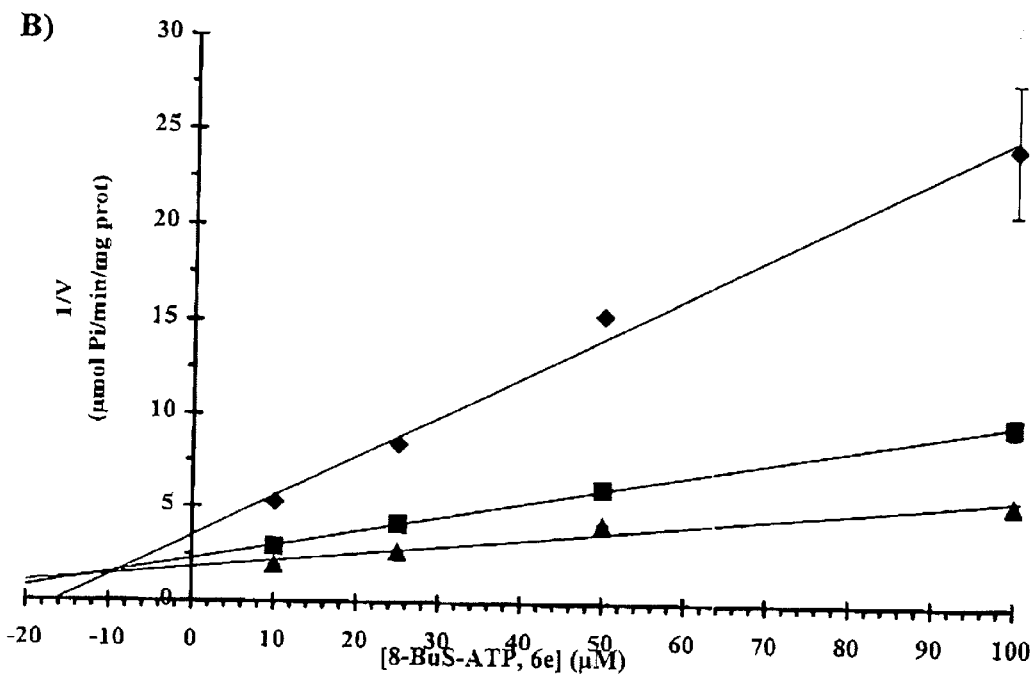
Figure 7A:
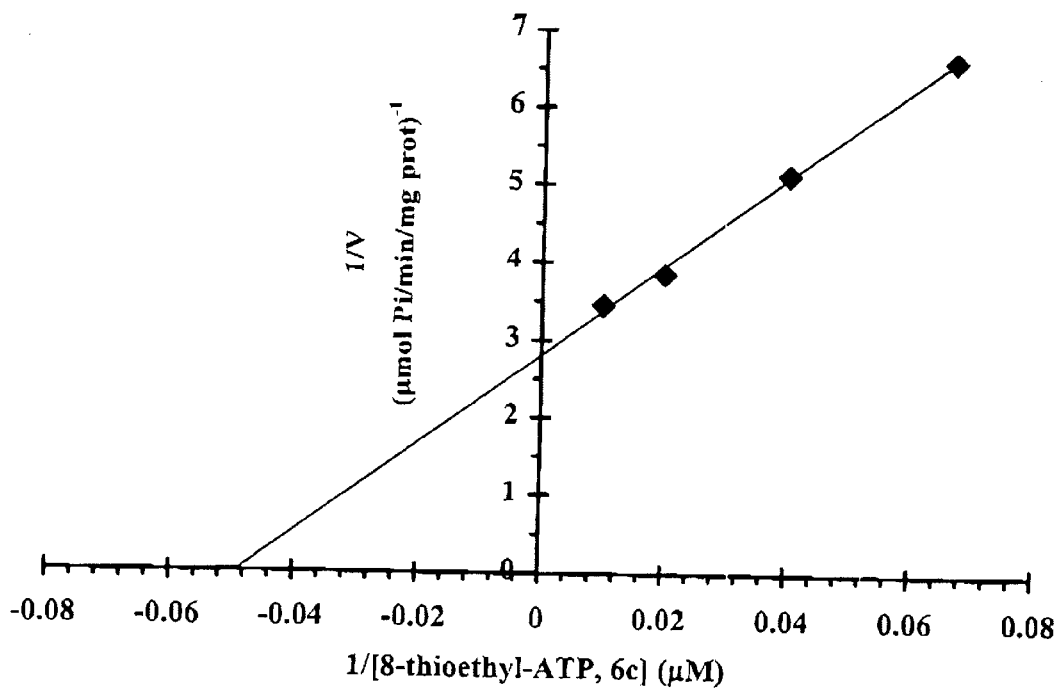
FIG. 7: A) Lineweaver-Burk representation of the hydrolysis of 8-thioethyl-ATP, 6c, by NTPDase. B) Dixon representations of 8-thiohexyl-ATP, 6d, inhibition. ATP concentration: 15 $\mu$M (♦) and 50 $\mu$M (■). Analog concentrations (0 to 100 $\mu$M). Analog 6d acts as a non-competitive inhibitor with an estimated Ki of 16 $\mu$M. Experiments was carried out in triplicate and expressed as the mean±SEM.

Analysis of NTPDase hydrolysis of ATP analogs. The ATP analogs substituted at positions C2 and C8, respectively, were first tested with respect to their resistance to NTPDase hydrolysis. The results obtained demonstrate that analogs substituted with electron donating groups at C8 were more resistant to hydrolysis than the corresponding C2 substituted analogs (FIG. 3). While a level of hydrolysis was observed with 8-Br-ATP, 8-BuNH-ATP, 7, 8-BuO-ATP, 8, and 8-ethylS-ATP, 6c (FIG. 7A), the compounds 8-cycloheptylS-ATP, 6a, 8-CH$_2$tBuS-ATP, 6b, 8-hexylS-ATP, 6d, and 8-BuS-ATP, 6e, were resistant to hydrolysis by NTPDase (FIG. 3). It is noteworthy that all the C2 substituted molecules displayed Km values in the range found for ATP and ADP (FIG. 4). This indicates that the affinity for the catalytic site is equivalent for all these analogs. Hence the position of the substituent is clearly important for resistance to the catalytic activity of the enzyme.

Hydrophobic interactions and H-bonds of the C2 substituent appear to be important determinants for P2Y-R ligand affinity. The conformational preference of the ligands in solution, determined by NMR experiments, may explain in part the differences in P2Y-R potency between the 2- and 8-substituted compounds. All 2-substituted derivatives possess an anti conformation, whereas the 8-ether and thioether analogs are in the syn conformation. The latter are apparently not tolerated by the tentative P2Y1-R binding-site (64–66). In contrast, the NTPDase active site can accommodate 8-thioetherATP analogs, and even derivatives bearing large or bulky substituents (8-CH$_2$tBuS-ATP, and 8-cycloheptylS-ATP and 8-hexylS-ATP), probably in their expected syn conformation. This conformation is likely unfavorable for catalytic activity, namely, the orientation of the triphosphate chain in the syn conformation is probably shifted away from the catalytic amino acid residues.

Figure 6A:
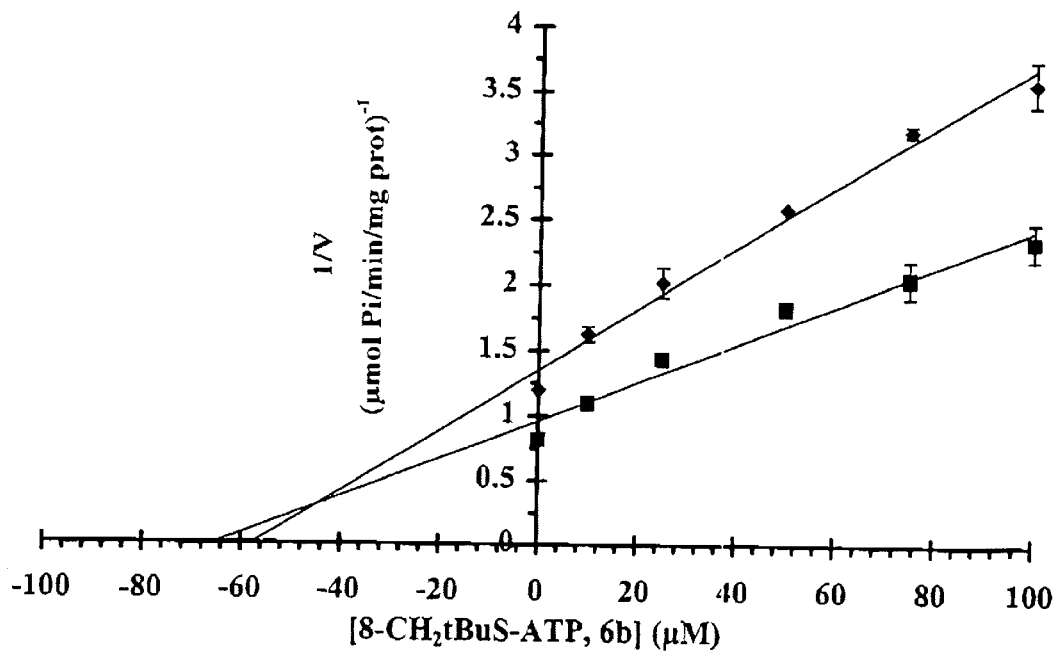
FIG. 6: Dixon representations of 8-$CH_2$tBuS-ATP, 6b, (panel A) and 8-cyclohepthylS-ATP, 6a, (panel B) inhibition. ATP concentration: 50 $\mu$M (♦) and 100 $\mu$M (■). Analog concentrations (0 to 100 $\mu$M). Both analogs act as mixed type inhibitors with estimated Ki of 45 and 31 $\mu$M for 8-t$BuCH_2$S-ATP, 6b, and 8-cyclohepthylS-ATP, 6a, respectively. Experiments were carried out in triplicate and expressed as the mean±SEM.
Figure 6B:
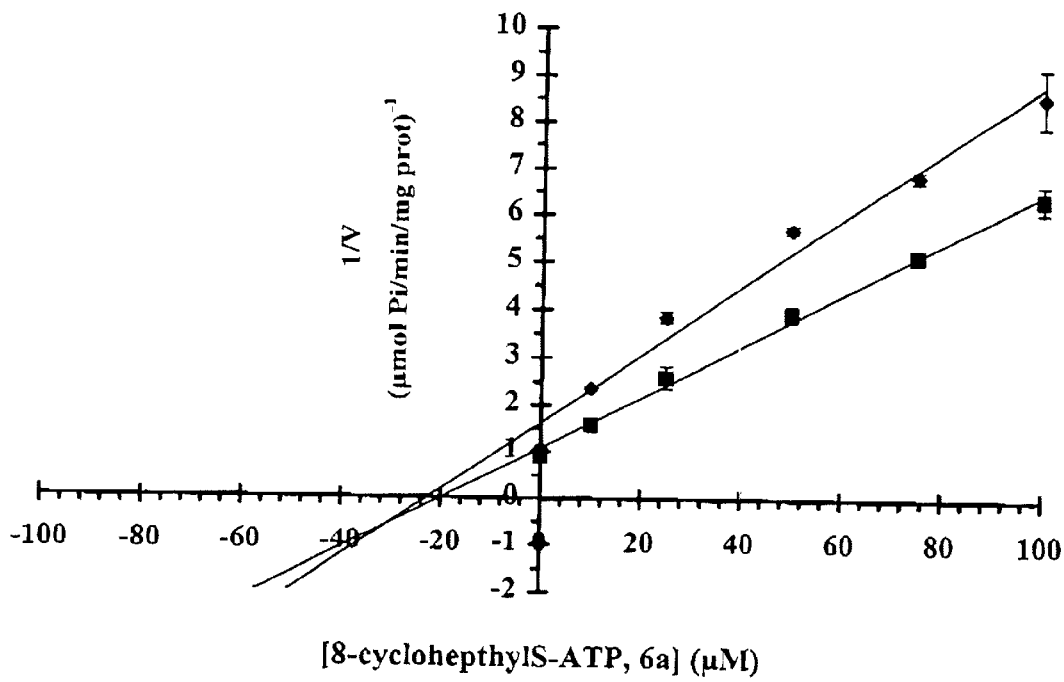
Figure 7B:
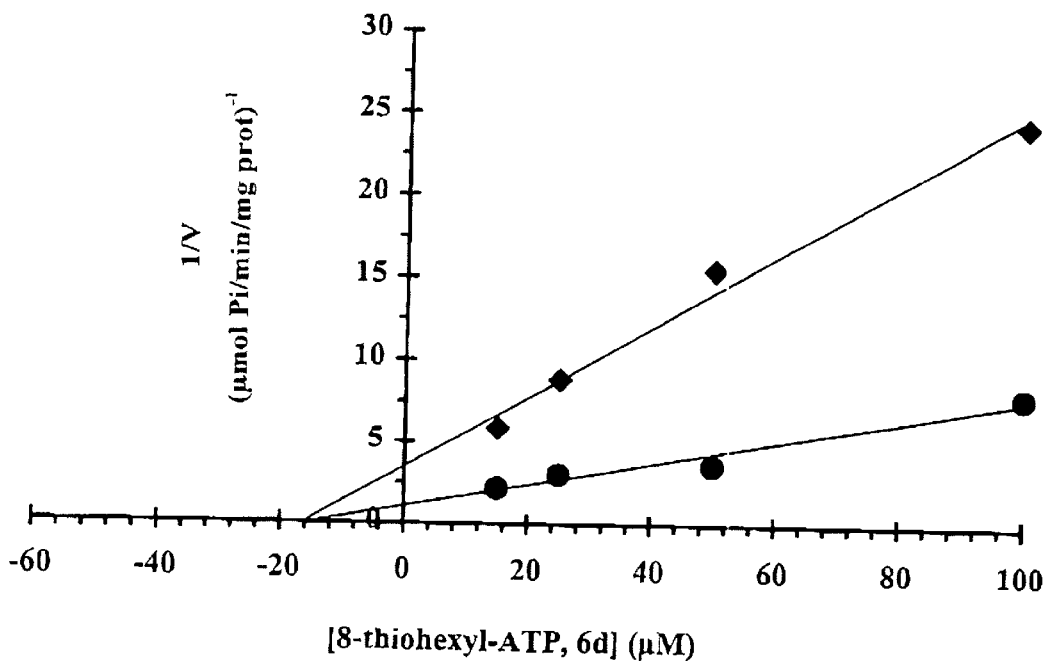

Analysis of potency of C8-substituted ATP analogs as NTPDase inhibitors. Having established that these 8-thioester ATP derivatives were not significantly hydrolyzed, they were then investigated in regard to their potency as NTPDase inhibitors (FIG. 3). One striking feature is that the four derivatives, 6a, b, d, e are good inhibitors (FIGS. 4–7). Again, the affinity (Ki) falls in the same range of affinity of that of ATP and ADP with one exception, the 8-$CH_2$tBuS-ATP, which has a slightly higher Ki (FIG. 4). However, even if these four analogs all display efficient NTPDase inhibition, 8-BuS-ATP, 6e, (FIG. 5) is to be considered as the preferred inhibitor, because it exhibits competitive inhibition with a Ki lower then those measured for compounds 6a, b, d, which are further less stable analogs with respect to NTPDase hydrolysis. The fact that this inhibitor (6e) interacts specifically with the binding site of the enzyme potentially reduces the risk of interference with other ATP-binding enzymes or receptors, and thus possesses a high degree of specificity. 8-$CH_2$tBuS-ATP, 6b, and 8-cycloheptylS-ATP, 6a, showed mixed types of inhibition thereby complicating the interpretation of their interaction with NTPDase (FIG. 6). Analog 6d exhibits non-competitive inhibition, thereby suggesting that its inhibitory effects are the results of an interaction with another part of the enzyme distinct from the catalytic site (FIG. 7B). From these results, it appears that the catalytic-site of NTPDase, may tolerate long and bulky substituents at the C8 position and also tolerate nucleotides in syn and anti conformations. It is noteworthy that the electronic nature of the modified purine ring has almost no influence on the affinity for the catalytic site, since thioether, aminoether and oxyether shows similar apparent affinity (Km or Ki) for the enzyme.

EXAMPLE 3

Analysis of Effects on P2-receptor Activity of Purine Nucleotide Analogs

Surgical Procedures. Dunkin-Hartley guinea pigs (300–350 g) of either sex were sacrificed by cerival dislocation according to the Canadian Council on Aminal Care. The guinea pig mesentery was prepared as described by Berthiaume et al (63). Briefly, the colic and ileocolic branches of the superior mesenteric artery were tied and the superior mesenteric artery cannulated (Portex size tube 3FG). To isolate the mesenteric bed from the intestine, the mesentery was perfused (2 ml/min, for 5 min) via the mesenteric artery with a Krebs solution containing heparin (100 U/ml). The mesentery was then separated by cutting close to the intestine. A resting period of 60 min was then allowed during which the guinea pig mesenteric bed was perfused (2 ml/min) with a warmed (37° C.) and gassed Krebs solution (95% $O_2$ and 5% $CO_2$) containing indomethacin (5 $\mu$M), as described earlier. In all the assays, perfusion pressure was increased to obtain a flow rate of 6 ml min$^{-1}$. Response of mesenteric bed, precontracted with noradrenaline (200 $\mu$M) in 0.9% saline solution, to the different drugs, was measured with a pressure transducer (Statham, model P-23AC) and recorded on a Grass physiograph (model 79D).

P2X-receptor assays. Guinea pig mesenteric bed was denuded from its endothelium layer by using 20 mM of CHAPS in PBS (63). Briefly, the CHAPS solution was infused for 45 sec, followed by a resting period of 30 min. Finally a second 45 sec infusion of 20 mM CHAPS was carried out. Blood vessels were then precontracted as earlier described. The efficiency of the endothelium removal technique was assessed by an intra-arterial bolus injection of 100 pmol of NK-1 in PBS. Reactivity of the media layer was confirmed by bolus injection of 3 nmol of NaNP (sodium nitroprussiate) in PBS. Bolus injections of increasing concentrations of 8-BuS-ATP (0.1 to 1000 pmol) in PBS, were administered. Variation of perfusion pressure were measured. Between each injection of 8-BuS-ATP a resting period was allowed to allow the return of pressure to baseline (i.e. precontracted pressure).

P2Y-receptor assays. Intact mesenteric bed vessels were precontracted with noradrenaline (200 $\mu$M). Mesentery was infused for 7 min with 7 $\mu$M of 8-BuS-ATP or PBS (control), followed by intra-arterial bolus injection of increasing concentrations of ATP (0.1 pmol to 10000 pmol). A resting period between each ATP injection was allowed to return to baseline, as described above. Blood vessel reactivity was assessed by a bolus injection of 3 nmol of NaNP. Response of the endothelium layer was confirmed by injection of NK-1 (100 pmol).

Statistics. Data are expressed as mean±SEM and number of replicates are in figure legends. Kinetic studies have been performed using Grafit software version 4 (Erithacus, UK). Unless stated otherwise, comparison between data was performed by one-way ANOVA test. Probability values of less than 0.05 were considered significant.

Figure 8A:
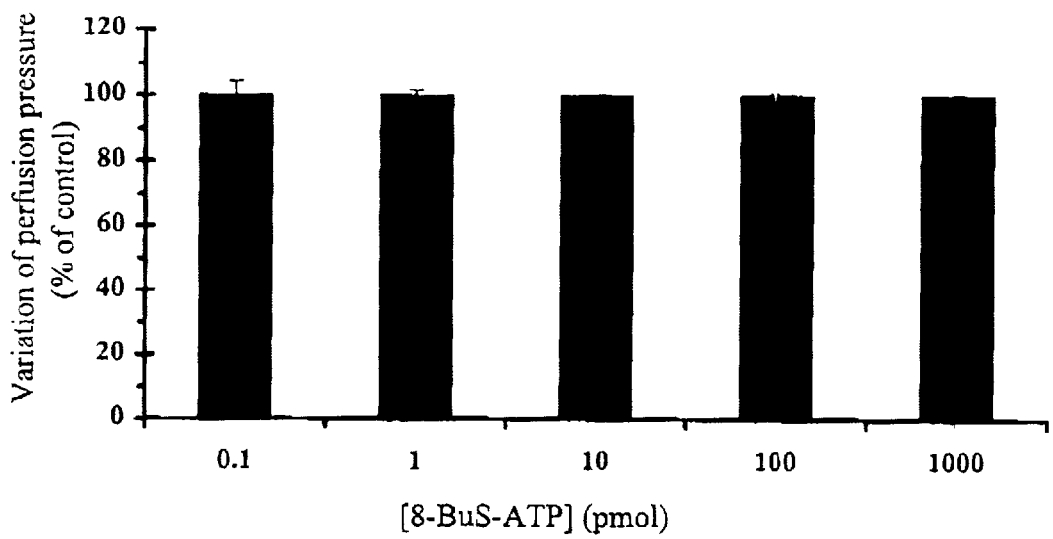
FIG. 8: Purinergic activity of 8-BuS-ATP, 6e.
Figure 8B:
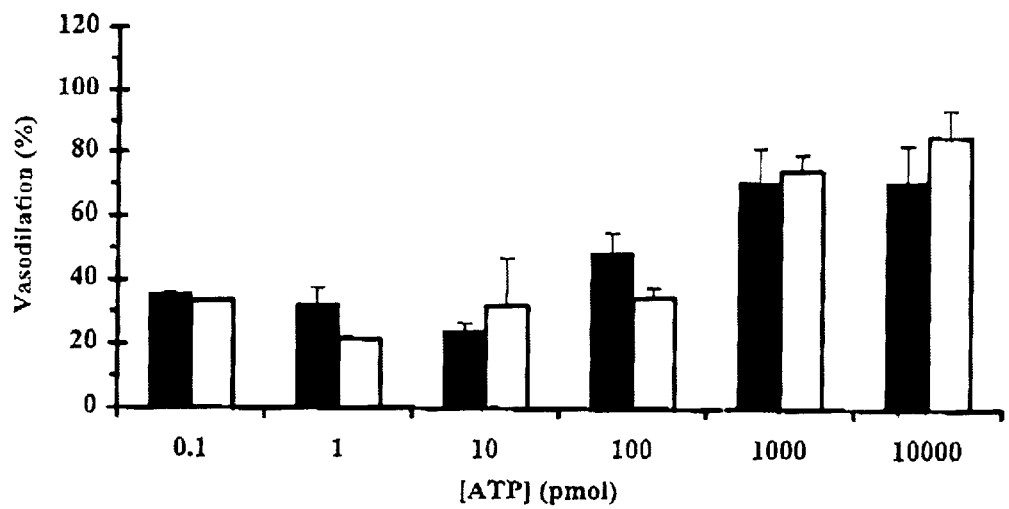

Effects on purinoceptor activity. Using the methods described above, the compounds of the invention were analyzed with respective to any effects on the activity of purinoceptors. Recent studies have indicated that 8-BuS-ATP was a poor agonist for P2Y$_1$ receptor. In rat astrocytes this compound has no effect on [$Ca^{2+}$]$_i$ level, whereas the corresponding 2-substituted ATP analogs potently increased [$Ca^{2+}$]$_i$ level. Similar results were obtained with turkey erythrocyte membranes (67). Since this molecule qualifies as a potent inhibitor, we tested its influence in the isolated mesenteric bed of the guinea pig for potential P2X and P2Y purinergic effects was tested (FIG. 8). Isolated guinea pig mesenteric artery and vein have been shown to respond to ATP via a P2X-purinoceptor located at the surface of the smooth muscle cells (68, 69). This latter purinoceptor was sensitive to $\alpha$, $\beta$-$CH_2$-ATP, 1b, a P2X agonist (70, 71). CHAPS was used to remove the blood vessel endothelium which gives rise to endothelium denuded vessels. Non-functional endothelium has been shown by a lack of response to 100 pmol of NK-1 (63). Our data show that 8-BuS-ATP was not able to initiate any P2X-R effect at concentrations up to 1000 pmol, indicating that it does not interact with P2X-R (FIG. 8A). We also evaluted the effect of an infusion of 8-BuS-ATP on the vasodilatory response induced by administration of increasing ATP concentrations (0.1 pmol to 10000 pmol), in intact mesenteric bed. Even in the presence of 7 $\mu$M 8-BuS-ATP the response to ATP was unmodified, confirming that 8-BuS-ATP did not interact with P2Y-R (FIG. 8B).

Figure 8C:
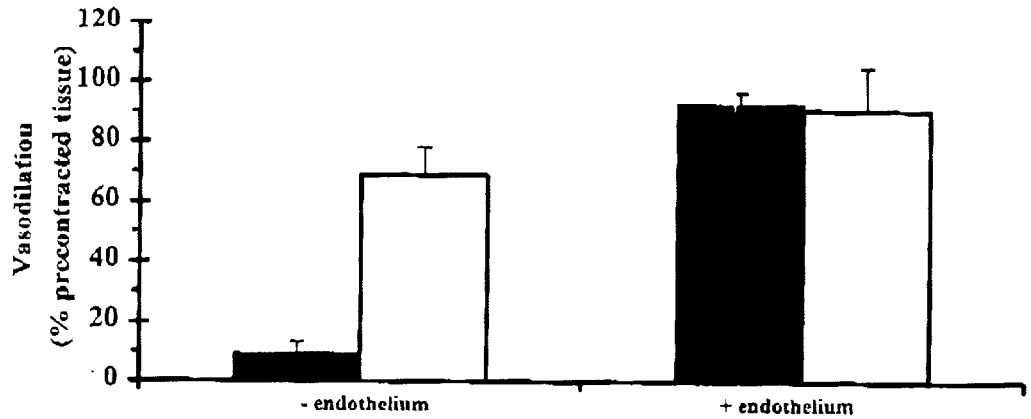

The integrity of the endothelium was assessed and confirmed with NK-1 and NaNP (FIG. 8C).

All of the references cited above and listed in the REFERENCES section below are herein incorporated by reference.

REFERENCES

1. Burnstock, G., Campbell, G., Bennett, M., and Holman, M. E. Int. J. Neuropharmacol 3: 163–166, 1964.
2. Burnstock, G. Evolution of the autonomic innervation of visceral and cardiovascular systems in vertebrates. Pharmacol. Rev. 21 (4): 247–324, 1969.
3. Su, C., Bevan, J. A., and Burnstock, G. [3H] adenosine triphosphate: release during stimulation of enteric nerves. Sciences 173(994): 336–338, 1971.
4. Langer, S. Z., and Pinto, J. E. B. Possible involvement of a transmitter different from norepinephrine in the residual responses to nerves stimulation of the cat nictitating membrane after pretreatment with reserpine. J. Pharmacol. Exp. Ther. 196(3): 697–713, 1976.
5. Burnstock, G. Purinergic receptors. J. Theor. Biol. 62 (2): 491–503, 1976.
6. Von Kugelgen, I., and Starke, K. Noradrenaline-ATP co-transmission in the sympathetic nervous system. Trends Pharmacol. Sci. 12(9): 319–324, 1991.
7. Westfall, D. P., Sedaa, K. O., Shinozuka, K., Bjun, R. A., and Buxton, I. L. Ann. NY Acad. Sci. 603: 300–310, 1990.
8. Burnstock, G. Neural nomenclature. Nature 229(5282): 284–283, 1971.
9. Burnstock. G. Purinergic receptors. J. Theor. Biol. 62 (2): 491–503, 1976.
10. Burnstock, G. A basis for distinguishing two types of purinergic receptors. In: Cell membrane receptors for drugs and hormones: A multidisciplinary approach. (Eds. R. W. Straub and L. Bolis), Raven press, New York. Pp. 108–118, 1978.
11. Fredholm, B. B., Abbracchio, M. P., Burnstock, G., Daly, J. W., Harden, T. K., Jacobson, K. A., Leff, P., and Willaims, M. Nomenclature and classification pf purinoceptors. Pharmacol. Rev. 46(2): 143–156, 1994.
12. Juul, B., Plesner, L., and Aalkjaer, C. Effects of ATP and related nucleotides on the tone of isolated rat mesenteric resistance arteries. J. Pharmacol. Exp. Therap. 264: 1234–1240, 1993.
13. Motte, S.; Commun, D.; Pirotton, S.; Boeynaems, J. M. Involvement of multiple receptors in the actions of extracellular ATP: the example of vascular endothelial cells. Int. J. Biochem. Cell Biol. 27: 1–7, 1995.
14. Rongen, G. A., Floras, J. S., Lender, J. W. M, Thier, T., and Smits, P. Cardiovascular pharmacology of purines. Clin. Sci. 92: 13–24, 1997.
15. Dubyak, G. R., and El Moatassim, C. Signal transduction via P2-purinergic receptors for extracellular ATP and other nucleotides. Am. J. Physiol. 265: C577–C606, 1993
16. Johnson, C. R., and Hourani, S. M. Contractile effects of uridine 5'-triphosphate in the rat duodenum. Br. J. Pharmacol. 113(4): 1191–1196, 1994.
17. Pennanen, M. F., Bass, B. L., Dziki, A. J., and Harmon, J. W. Adenosine differential effect on blood flow to suregions of the upper gastrointestinal tract. J. Surg. Res. 56(5): 461–465, 1994.
18. Strohmeier, G. R., Reppert, S. M., Lencer, W. I., and Madana, J. L. The $A_{2b}$ adenosine receptor mediated cAMP responses to adenosine receptor agonists in human intestinal epithelia. J.Biol. Chem. 270(5): 2387–2394, 1995.
19. Hancock, D. L., and Coupar, I. M. Functional characterization of the adenosine receptor mediating inhibition of peristalsis in the rat jejunum. Br. J. Pharmacol 115(5):739–744, 1995.
20. Sarna, S. K. Gastrointestinal longitudinal muscle contractions. Am J. Physiol. 265(lptl): G156–G164, 1993.
21. Baricordi, O. R., Ferrari, D., Melchiorri, L., Chiozzi. P., Hamann, S., Chiair, E., Ribini, M., and Di Virgilio, F. An ATP-activated channel is involved in mitogenic stimulation of human T lumphocytes. Blood 87(2): 682–690, 1996.
22. Di Virgilio, F. The P2Z purinoceptor: an intriguing role in immunity, inflammation and cell death. Immunol. Today 16(11): 525–528, 1995.
23. Ventura, M. A., and Thomopolous, P. ADP and ATP activate distinct signaling pathways in human promonocytic U-937 cells differentiated with 1,25-dihydroxy-vitamin D3. Mol. Pharmacol 47: 104–114, 1995.
24. Biffen, M., and Alexander, D. R. Mobilization of intracellular $Ca2+$ by adenine nucleotides in human T-leukaemia cells: evidence for ADP-specific and P2y-purinergic receptors. Biochem. J. 304:769–774, 1994.
25. Apasov, S., Koshiba. M., Redegeld, F., and Sitokovsky, M. V. Role of extracellular ATP and P1 and P2 classes of purinergic receptors in T-cell development and cytotoxic T lymphocyte effector functions. Immunol. Rev. 146: 5–19, 1995.
26. Hedge, S. S., Mandel, D. A., wilfird, M. R., Briand, S., Ford, A. P. D. W., and Eglen, R. M. Evidence for purinergic neutransmission in the uninary bladder of pithed rats. Eur. J. Pharmacol. 349(1): 75–82, 1998.
27. Dunwiddic, T. V., Abbracchio, M. P., Bischofberger, N., Brundege, J. M., Bruell, G., Collo, G., Corsi, C., Diao, L., Kawashima, E., Jacobson, K. A., Latini, S., Lin, R. C. S., Noth, R. A., Pazzagli, M., Pedata, F., Pepen, G. C., Proctor, W. R., Rassendren, F., Surprenant, A., and Cattabeni, F. Purinoceptors in the central nervous system. Drug Dev. Res. 39(3–4): 361–370, 1996.
28. Burnstock, G., and Wood, J. N. Purinergic receptors—Their role in nociception and primary afferent neurotransmission. Curr. Opinion in Neurobiol. 6(4): 526–532, 1996.
29. Von Kugelgen, I. Purinoceptors modu;ating the release of noradrenaline. J. Autonomic. Pharmacol. 14(1): 11–12, 1994.
30. Beaudoin, A. R.; Sévigny, J.; Picher, M. ATP diphosphohydrolases, apyrases and nucleotide phosphohydrolases: biochemical properties and functions. In: Biomembrane, vol. 5; Lee, A. G., Ed.; Greenwich, Conn.: JAI, pp. 369–401, 1996.
31. Beaudoin, A. R.; Grondin, G.; Enjyoji, K.; Robson, S. C.; Sévigny, J.; Fischer, B., Gendron, F.-P. Physiological role of NTPDases (ATP diphosphohydrolases) in mammals. Proceeding of the $2^{nd}$ International Workshop on ecto-ATPase and related nucleotidases. Diepenbeek, Belgium, Jun. 14–18, 1999. Vanduffel L., and Lemmens R., Eds. Shaker Publishing B. V., The Netherlands; pp. 125–135, 2000.
32. Plesner, L. Ecto-ATPases: identities and functions. Int. Rev. Cytol. 158: 141–214, 1995.
33. Vlajkovic, S. M.; Thorne, P. R.; Hously, G. D.; Munoz, D. J. B.; Kendrick, I. S. Ecto-nucleotidases terminate purinergic signalling in the cochlear endolymphatic compartment. Neuroreport 9: 1559–1565, 1998.
33. Zimmermann, H. 5'-Nucleotidase: molecular structure and functional aspects. Biochem. J. 285: 345–365, 1992.
34. Laliberté, J. F., and Beaudoin A R. Sequential hydrolysis of the gamma- and beta-phosphate groups of ATP by the ATP diphosphohydrolase from pig pancrease. Biochim. Biophys Acta. 742(1):9–15, 1983.

35. Côté Y. P., Pavate C. and Beaudoin A. R. The control of nucleotides in blood vessels: Role of the ATP diphosphohydrolase (apyrase). Curr. Top. Pharmacol. 1: 83–92, 1992.

37. Sévigny J., Levesque F. R., Grondin G. and Beaudoin A. R. Purification of the blood vessel ATP diphosphohydrolase, identification and localization by immunological techniques. Biochim. Biophys. Acta 1334: 73–88, 1997.

38. LeBel, D., Poirier G. G. Phaneuf, S. St-Jean P., Laliberté and Beaudoin A. R. Characterization and purification of a calcium sensitive ATP diphosphohydrolase from the pig pancrease. J. Biol. Chem. 255: 1227–1233, 1980.

39. Sévigny, J.; Côté, Y. P.; Beaudoin, A. R. Purification of pancrease type I ATP diphosphohydrolase and identification by affinity labelling with 5'-p-fluorosulfonyl benzoyl adenosine ATP analog. Biochem. J. 312: 351–356, 1997.

40. Sévigny J., Levesque F. R., Grondin G. and Beaudoin A. R. Purification of the blood vessel ATP diphosphohydrolase, identification and localization by immunological techniques. Biochim. Biophys. Acta 1334: 73–88, 1997.

41. Christoforidis, S.; Papamarcaki, T.; Galaris, D.; Kellner, R.; Tsolas, O. Purification and properties of human placental ATP diphosphohydrolase. Eur. J. Biochem. 234: 66–74, 1995.

42. Kaczmarek, E.; Koziack, K.; Sévigny, J.; Siegel, J. B.; Anrather, J.; Beaudoin, A. R.; Bach, F. H.; Robson, S. C. Identification and characterization of CD39/vascular ATP diphosphohydrolase. J. Biol. Chem. 271: 33116–33122, 1996.

43. Maliszewski, C. R.; Delespesse, G. L.; Schoenborn, M. A.; Armitage, R. J.; Fanslow, W. C.; Nakajima, T.; Baker, E.; Sutherland, G. R.; Poindexter, K.; Birks, C.; Alpert, A.; Friend, D.; Gimpel, S. D.; Gayle III, R. B. The CD39 lymphoid cell activation antigen: Molecular cloning and structural characterization. J. Immunol. 153: 3574–3583, 1994.

44. Wang, T. F.; Guidotti, G. CD39 is an ecto-(Ca2+, Mg2+)-apyrase. J. Biol. Chem. 271: 9898–9901, 1996.

45. Barcellos, C. K. Schetinger M R. Battastini A M. Silva L B. Dias R D. Sarkis J J. Inhibitory effect of cadmium acetate on synaptosomal ATP diphosphohydrolase (EC 3.6.1.5; apyrase) from adult rat cerebral cortex. Br. J. Med and Biol. Res. 27(5): 1111–1115, 1994.

46. Côté, Y. P., Ouellet, S., and Beaudoin, A. R. Kinetic properties of type-II ATP diphosphohydrolase from the tunica media of the bocine aorta. Biochim. Biophys. Acta 1160(3): 246–250, 1992.

47. Picher, M.; Sévigny, J.; D'Orleéans-Juste, P.; Beaudoin, A. R. Hydrolysis of P2-purinoceptor agonists by a purified ectonucleotidase from the bovine aorta, the ATP diphosphohydrolase. Biochem. Pharmacol. 51: 1453–1460, 1996.

48. Westfall, T. D., Kennedy, C., and Sneddon, P. The ecto-ATPase inhibotors ARL 67156 enhance parasympathetic neurotransmission in the guinea-pig urinary bladder. Eur. J. Pharmacol. 329(2–3): 169–173, 1997.

49. Crack, B. E., Pollard, C. E., Beukers, M. W., Roberts, S. M., Hunt, S. F., Ingall, A. H., McKechnie, K. C., Ijzerman, A. P., and Leff, P. Pharmacological and biochemical analysis of FPL 67156, a novel, selective inhibitor of ecto-ATPase. Br. J. Pharmacol. 114(2): 475–481, 1995.

50. Chen, B. C., Lee, C. M., and Lin W. W. Inhibition of ecto-ATPase by PPADS, suramin and reactive blue in endothelial cells, C-6 glioma cells and raw 264.7 macrophages. Br. J. Pharmacol. 119(8): 1628–1634, 1996.

51. Kennedy, C., Westfall, T. D., and Sneddon, P. Modulation of purinergic neurotransmission by ecto-ATPase. Sem. Neurosci. 8(4): 195–199, 1996.

52. Fischer, B.; Chulkin, A.; Boyer, J. L.; Harden, K. T.; Gendron, F.-P.; Beaudoin, A. R.; Chapal, J.; Hillaire-Buys, D.; Petit, P. 2-thioether-5'-O-(1-thiotriphosphate) adenine derivatives as new insulin secretagogues acting through P2Y-receptors. J. Med. Chem. 42: 3636–3646, 1999.

53. Bültmann, R., Wittenburg, H., Pause, B., Kurz, G., Nickel, P., and Starke, K. P2-purinoceptors antagonists: III. Blockade of P2-purinoceptor subtypes and ecto-nucleotidases by compounds related to suramin. Naunyn-Schmiedeberg's Arch. Pharmacol. 354: 498–504, 1996.

54. Tuluc, F., Bültmann, R., Glänzel, M., Wilhelm Frahm, A., and Starke, K. P2-receptor antagonists: IV. Blockade of P2 receptor subtypes and ecto-nucleotidases by compounds related to reactive blue 2. Naunyn-Schmiedeberg's Arch. Pharmacol. 357: 111–120, 1998.

55. Bültmann, R., and Starke, K. Reactive red 2: a P2Y-selective purinoceptor antagonist and an inhibitor of ecto-nucleotidase. Naunyn-Schmiedeberg's Arch. Pharmacol. 352: 477–482, 1995.

56. Wittenburg, H., Bültmann, R., Pause, B., Ganter, C., Kurz, G., and Starke, K. P2-purinoceptor antagonists: II. Blockade of P2-purinoceptor subtypes and ecto-nucleotidases by compounds related to Evans Blue and trypan blue. Naunyn-Schmiedeberg's Arch. Pharmacol. 354: 491–497, 1996.

57. Bültmann, R., Pause, B., Wittenburg, H., Kurz, G., and Starke, K. P2-purinoceptor antagonists: I. Blockade of P2-purinoceptor subtypes and ecto-nucleotidases by small aromatic isothiocyanto-sulphonates. Naunyn-Schmiedeberg's Arch. Pharmacol. 354: 481–490, 1996.

58. Bonan, C. D., Battastini, A. M. O., Schetinger, M. R. C., Moreira, C. M., Frassetto, S. S., Dias, R. D., and Sarkis, J. J. F. Effects of 9-amino-1,2,3,4-tetrahydroacridine (THA) on ATP diphosphohdrolase (EC 3.6.1.5) and 5' nucleotidases (EC 3.1.3.5) from rat brain synaptosomes. Gen. Pharmac. 28(5): 761–766, 1997.

59. Gendron, F.-P., Halbfinger E., Fischer B., D'Orleans-Juste P., Duval M. and Beaudoin, A. R. Novel ATP diphosphydrolase inhibitors: Synthesis, biochemical and pharmacological characterization. J. Med. Chem., 2000. (in press).

60. Fischer, B.; Boyer, J. L.; Hoyle, C. H.; Ziganshin, A. U.; Brizzolara, A. L.; Knight, G. E.; Zimmet, J.; Burnstock, G.; Harden, T. K.; Jacobson, K. A. Identification of potent, selective P2Y-purinoceptor agonists: structure-activity relationships for 2-thioether derivatives of adenosine 5'-triphosphate. J. Med. Chem. 36: 3937–3946, 1993.

61. Baykov A. A., Evtushenko O. A. and Avaeve S. M. Malachite green procedure for orthophosphate determination and its use in alkaline phosphatase-based enzyme immunoassay. Anal. Biochem. 171: 266–270, 1988.

62. Bradford M. M. A rapid and sensitive method for the quantification of microgram quantities of protein utilising the principle of protein-dye binding. Anal. Biochem. 72: 248–254, 1976.

63. Berthiaume, N.; Claing, A.; Regoli, D.; Warner, T. D.; D'Orléans-Juste, P. Characterization of receptors for kinins and neurokinins in the arterial and venous mesenteric vasculatures of the guinea-pig. Br. J. Pharmacol. 115: 1319–1325, 1995.

64. Halbfinger, E.; Major, D. T.; Ritzmann, M.; Ubl, J.; Reiser, G.; Boyer, J. L.; Harden, K. T.; Fischer, B. Molecular recognition of modified adenine nucleotides by the P2Y$_1$-receptor. Part I. A synthetic, biochemical, and NMR approach. J. Med. Chem. 42: 5325–5337, 1999.

65. Major, D. T.; Halbfinger, E.; Fischer, B. Molecular recognition of modified adenine nucleotides by the P2Y1-receptor. II. A computational approach. J. Med. Chem. 42: 5338–5347, 1999.

66. Van Rhee, A. M.; Fischer, B.; Van Galen, P. J. M.; Jacobson, K. A. Modelling the P2Y purinoceptor using rhodopsin as template. Drug Design and Delivery 13: 133–154, 1995.

67. Fischer, B.; Chulkin, A.; Boyer, J. L.; Harden, K. T.; Gendron, F.-P.; Beaudoin, A. R.; Chapal, J.; Hillaire-Buys, D.; Petit, P. 2-thioether-5'-O-(1-thiotriphosphate) adenine derivatives as new insulin secretagogues acting through P2Y-receptors. J. Med. Chem. 42: 3636–3646, 1999.

68. Hirst, G. D. S.; Jobling, P. The distribution of γ-adrenoceptors and P2 purinoceptors in mesenteric arteries and vains of theguinea-pig. Br. J. Pharmacol. 96: 993–999, 1989.

69. Onaka, U.; Fujii, K.; Abe, I.; Fujishima, M. Enhancement by exogenous and locally generated angiotensin II of purinergic neurotransmission via angiotensin type 1 receptor in the guinea-pig isolated mesenteric artery. Br. J. Pharmacol. 122: 942–948, 1997.

70. Fujii, K. Evidence for adenosine triphosphate as an excitatory transmitter in guinea-pig, rabbit and pig urinary bladder. J. Physiol. 404: 39–52, 1989.

71. Ishikawa, S. Actions of ATP and α, β-methylene ATP on neuromuscular transmission and smooth muscle membrane of the rabbit and guinea-pig mesenteric arteries. Br. J. Pharmacol. 86: 777–787, 1985.

What is claimed is:

1. A C8-substituted adenine nucleotide, wherein the adenine nucleotide is substituted at the C8 position with a thioether substituent, wherein the thioether substituent has the structure:

$$-S-X;$$

wherein X is selected from the group consisting of:
 (a) $C_7H_{13}$ (cycloheptyl)
 (b) $(CH_3)_3CCH_2$; and
 (c) $CH_3(CH_2)_n$, wherein $1 \leq n \leq 5$.

2. The adenine nucleotide of claim 1 selected from the group consisting of compound 6a, compound 6b, compound 6c, compound 6d and compound 6e.

3. The adenine nucleotide of claim 1, wherein n is selected from the group consisting of 1, 3 and 5.

* * * * *